(12) United States Patent
Sridhar et al.

(10) Patent No.: US 8,655,601 B1
(45) Date of Patent: Feb. 18, 2014

(54) METHOD AND SYSTEM FOR DETECTING PHOSPHORUS IN SOIL FROM REFLECTED LIGHT

(75) Inventors: B. B. Maruthi Sridhar, Bowling Green, OH (US); Robert K. Vincent, Bowling Green, OH (US)

(73) Assignee: Bowling Green State University, Bowling Green, OH (US)

( * ) Notice: Subject to any disclaimer, the term of this patent is extended or adjusted under 35 U.S.C. 154(b) by 772 days.

(21) Appl. No.: 12/658,533

(22) Filed: Feb. 8, 2010

(51) Int. Cl.
*G01N 31/00* (2006.01)

(52) U.S. Cl.
USPC ............................... 702/23; 702/30; 356/301

(58) Field of Classification Search
USPC .............. 702/22, 23, 27, 28, 30, 31; 356/301, 356/303
See application file for complete search history.

(56) References Cited

U.S. PATENT DOCUMENTS

| | | | |
|---|---|---|---|
| 3,761,713 A | 9/1973 | Merrill | |
| 4,310,758 A | 1/1982 | Peterson | |
| 4,495,416 A | 1/1985 | Mason et al. | |
| 4,864,127 A | 9/1989 | Barme | |
| 5,140,527 A | 8/1992 | Jones et al. | |
| 5,316,950 A | 5/1994 | Apitz et al. | |
| 5,323,317 A | 6/1994 | Hampton et al. | |
| 5,462,357 A | 10/1995 | Ingram et al. | |
| 5,512,834 A | 4/1996 | McEwan | |
| 5,686,314 A | 11/1997 | Miyazaki | |
| 5,764,819 A | 6/1998 | Orr et al. | |
| 5,887,491 A * | 3/1999 | Monson et al. | ............ 73/864.74 |
| 6,792,684 B1 | 9/2004 | Hyyppa | |
| 7,132,254 B2 | 11/2006 | Vincent | |
| 7,671,336 B2 * | 3/2010 | Jahn et al. | ................. 250/339.11 |
| 2005/0164332 A1 | 7/2005 | Vincent | |
| 2005/0164333 A1 | 7/2005 | Vincent | |
| 2007/0013908 A1* | 1/2007 | Lee et al. | ....................... 356/301 |
| 2007/0065857 A1 | 3/2007 | Glaser et al. | |
| 2008/0260237 A1 | 10/2008 | Savolainen et al. | |
| 2009/0039255 A1 | 2/2009 | Andrews et al. | |
| 2009/0287520 A1 | 11/2009 | Zimmerman | |
| 2010/0098342 A1 | 4/2010 | Davis et al. | |
| 2010/0100835 A1 | 4/2010 | Klaric et al. | |

OTHER PUBLICATIONS

Abrams, M.J., et al., Remote Sensing for Porphyry Copper Deposits in Southern Arizona, Economic Geology, (1983), vol. 78, 591-604.
Yamaguchi, Y., Possible Techniques for Lithologic Discrimination Using the Short-Wavelength-Infrared Bands of the Japanese ERS-1, Remote Sensing of Environment, (1987), vol. 23, 117-129.
Amato, I., Remote Sensing: A Distant View of Chemisty, Analytical Chemistry, (1988), vol. 60, 1339A-1344A.
Crowley, J.K., et al. Airborne Imaging Spectrometer Data of the Ruby Mountains, Montana: Mineral Discrimination Using Relative Absorption Band-Depth Images, Remote Sensing of Environment, (1989), vol. 29, 122-134.

(Continued)

*Primary Examiner* — Manuel L Barbee
(74) *Attorney, Agent, or Firm* — Marshall & Melhorn LLC

(57) ABSTRACT

The present invention relates to a method of detecting soil nutrients or soil nutrients in soil from reflected light, and also includes systems for the measurement, calculation and transmission of data relating to or carrying out that method.

18 Claims, 8 Drawing Sheets
(8 of 8 Drawing Sheet(s) Filed in Color)

(56) References Cited

OTHER PUBLICATIONS

Wester, K., et al. Analytically Processed Landsat TM Images for Visual Geological Interpretation in the Northern Scandinavian Caledonides, ISPRS Journal of Photogrammetry and Remote Sensing, (1990), vol. 45, 442-460.
Spatz, D.M., et al. Exploration for Copper-Molybdenum-Gold Porphyry Deposits Using Multispectral and Hyperspectral Aerospace Remote Sensing Techniques, Proceedings ISPRS Commission Symposium on Resource and Environmental Monitoring, vol. 30, part 7a, Rio de Janeiro, Brazil, IMPE, San Jose dos Campos, 460-473.
Spatz, D., Remote Sensing Strategies in Mineral Exploration and Development: The Precious Metal and Porphyry Deposit Models, International Archives of Photogrammetry and Remote Sensing, (1994), vol. 31, part B7, Vienna, Austria, (1996) 638-649.
Taranik, J.V., et al., Remote Sensing for Geology and Mineral Resources, an Assessment of Tools for Geoscientists in the Future, International Archives of Photogrammetry and Remote Sensing, 1996), vol. 31, part B7, Vienna Austria, (689-698.
Sommer, S., et al., The Potential of Remote Sensing for Monitoring Rual Land Use Changes and Their Effects on Soil Conditions, Agriculture, Ecosystems and Environment, (1998), vol. 67, 197-209.
Sabins, F., Remote Sensing for Mineral Exploration, Ore Geology Reviews, (1999), vol. 14, 157-183.
Abdelsalam, MG., et al., Mapping Gossans in Arid Regions With Landsat TM and SIR-C Images: The Beddaho Alteration Zone in Northern Eritrea, Journal of African Earth Science, (2000), vol. 30, 903-916.
Ramapriyan, H.K., Satellite Imagery in Earch Science Applications, Image Databases: Search and Retrieval of Digital Imagery, Edited by V. Castelli, et al. (2002), John Wiley & Sons, Inc., New York, 35-82.
Ben-Dor, E., Quantitative Remote Sensing of Soil Properties, Advances in Agronomy, (2002), vol. 75, 173-243.
Kemper, T., et al., Estimate of Heavy Metal Contamination in Soils After a Mining Accident Using Reflectance Spectroscopy, Environmental Science and Technology, (2002), vol. 36, 2742-2747.
Ninomiya, Y., A Stablized Vegetation Index and Several Mineralogic Indices Defined for Aster VNIR and SWIR Data, International Geoscience and Remote Sensing Symposium (IGARSS'03), (2003), vol. 3 Toulouse, France, 1552-1554.
Ramadan, T.M., et al., Mineralogical and Structural Characterization of Alteration Zones Detected by Orbital Remote Sensing At Shalatein District, Se Desert, Egypt, Journal of African Earth Sciences, (2004), vol. 40, 89-99.
Bogrekci, I., et al., Spectral Soil Signatures and Sensing Phosphorus, Biosystems Engineering, (2005), vol. 92, 527-533.
Farifteh, J., et al., Assessing Salt-Affected Soils Using Remote Sensing, Solute Modelling, and Geophysics, Geoderma, (2006), vol. 130, 191-206.
Mars, J.C., et al., Regional Mapping of Phyllic- and Argillic-Altered Rocks in the Zagros Magmatic ARC, Iran, Using Advanced Spaceborne Thermal Emission and Reflection Radiometer (Aster) Data and Logical Operator Algorithms, Geosphere, (2006), vol. 2, 161-186.
Cloutis, E.A., et al., Detection and Discrimination of Sulfate Minerals Using Reflectance Spectroscopy, Icarus, (2006), vol. 184, 121-157.
Moghtaderi, A., et al., The Application of Advanced Space-Borne Thermal Emission and Reflection (Aster) Radiometer Data in the Detection of Alteration in the Chadormalu Paleocrater, Barq Region, Central Iran, Journal of African Earth Sciences, (2007), vol. 30, 238-252.
Bogrekci, et al., Comparison of Ultraviolet, Visible, and Near Infrared Sensing for Soil Phosphorus, Biosystems Engineering, (2007), vol. 96, 293-299.
Boonchom, B., et al., Rapid Coprecipitation and Non-Isothermal Decomposition Kinetics of New Binary $Mn_{0.5}Cu_{0.5}(H_2PO_4)_2$-1.$5H_2O$, Industrial Engineering and Chemical Research, (2008), vol. 47, 2941-2947.
Choe, E., et al., Mapping of Heavy Metal Pollution in Stream Sediments Using Combined Geochemistry, Field Spectroscopy, and Hyperspectral Remote Sensing: A Case Study of the Rodalquilar Mining Area, SE Spain, Remote Sensing of Environment, (2008), vol. 112, 3222-3233.
Tetra Tech EM Inc., Final Cercla Emergency Response Report, Kingston Fossil Plant Fly Ash Response Harriman, Roane County, Tennessee (Soil and Ash Sampling Results), URL: http://www.epaosc.org/sites/4642/files/erfinalreporttvakingston.pdf, (2009).
Sridhar, B.B, et al., Mapping the Total Phosphorus Concentration of Biosolid Amended Surface Soils Using Landsat TM Data, (Science of the Total Environment, (2009), vol. 407, 2894-2899.
Sridhar, B.B., et al., Mapping and Estimation of Phosphorus and Copper Concentrations in Fly Ash Spill Area Using Landsat TM Images, Photogrammetric Engineering and Remote Sensing, (2009), vol. 75, 1030-1033.

* cited by examiner

METHOD AND SYSTEM FOR DETECTING PHOSPHORUS IN SOIL FROM REFLECTED LIGHT

STATEMENT REGARDING GOVERNMENTAL INTEREST

The present invention was made through funding from grant numbers 10390042/-0048/-0050 from the US Department of Agriculture (USDA). The United States Government has certain rights in the invention.

FIELD OF THE INVENTION

The present invention relates to a method of detecting nutrients in soil from reflected light.

BACKGROUND AND SUMMARY OF THE INVENTION

Conventional methods for soil sampling and analysis for soil variability in chemical characteristics are too time-consuming and expensive for multi-seasonal monitoring over large-scale areas.

In many instances it is desirable to be able to detect the presence of nutrients in soil, particularly phosphorus, which can enrich nearby lakes in phosphorus via surface water runoff, thereby promoting cyanobacteria blooms in lakes. Showing where soils are less enriched in nutrients also can be used in precision farming to direct the farmer to add only the necessary amount of nutrients when fertilizing soils, thereby reducing the cost of fertilizer to the farmer and reducing the nutrient load added to nearby lakes from surface water run-off from farm fields.

It is particularly desirable to be able to detect the presence of nutrients in soil in a manner that is convenient and provides relatively immediate results so that the public, farmers or agricultural authorities may be warned or other actions taken to avoid or eliminate contamination of the assayed soil.

Application of treated sewage sludges (biosolids) to agricultural land has become a prominent and acceptable method of waste disposal in recent years. Biosolids are known to improve soil physical characteristics (Epstein et al., 1975; Wei et al., 1985), increase the organic matter and cation exchange capacity and supply the nutrients required for crop growth (Sommers, 1977; Singh and Agrawal, 2008). However, the potential for excess application of biosolids, resulting in a build up of nitrogen, phosphorus (Mantovi et al., 2005), zinc, copper, lead (Mantovi et al., 2005; Udom et al., 2004; Nyamangara and Mzezewa, 1999) and cadmium (Bergkvist et al., 2003) in the surface soils of agricultural fields continues to be an area of concern. Other types of fertilizers can build up the nutrients in soils to an impractical, potentially harmful level. Accumulation of phosphorus at high concentrations is a major environmental concern, as it affects the water quality of lakes and rivers in the event of runoff (Shober and Sims, 2003).

Hence, there is an increasing need to continuously monitor the extent of soil contamination in biosolid-applied fields, and in other types of fertilized fields, also. Even though conventional methods of soil sampling and testing are being used for this purpose, they are often expensive, time-consuming and unsuitable for mapping soil contamination over large areas.

Remote sensing has been used as an alternative method for determining and mapping the physical and chemical characteristics of the soil. High resolution aerial imagery was used to map the organic carbon (Chen et al., 2000), clay content (Sullivan et al., 2005), organic matter and Bray-1 phosphorus concentration (Varvel et al., 1999) in bare soils. Dematte et al. (2003) reported that chemical variations in soil resulting from fertilizer applications can be detected, based on the intensity of reflectance. Several studies showed the use of spectral reflectance to determine the soil color (Post et al., 2000), texture and particle size distribution (Chang et al., 2001), soil moisture (Lobell and Asner, 2002), iron oxides (Ji et al., 2002), carbonates (Ben-Dor and Banin, 1990), clay (Ben-Dor and Banin, 1995), organic carbon (Dalal and Henry, 1986; Morra et al., 1991; Reeves et al., 2002) organic matter (Henderson et al., 1992) and soil phosphorus (Bogrekci and Lee, 2005, 2007).

As used herein, remote sensing refers to the capability of obtaining information about an object without touching it. Sensors which are not in direct contact with the object are generally used to obtain the information. In a more limited context, the information obtained by remote sensing is a function of energy emitted by, absorbed by, or reflected from the object.

As used herein, where the remote sensing is conducted from distances from which vegetation may cover portions of the soil surface, vegetation may be excluded according to a masking formula, such as elimination from consideration of any areas that exceed a lower threshold of the Normalized Difference Vegetation Index (NDVI) standard, which is a simple numerical indicator that can be used to analyze remote sensing measurements, typically but not necessarily from a space platform, and assess whether the target being observed contains live green vegetation or not. This may be arrived at by using LANDSAT TM bands 3 and 4 in a formula (4−3)/(4+3) to arrive at a value that is broadly between 0.1 and 0.3, preferably about 0.2. Regions above this threshold range would be blacked out or otherwise eliminated from the algorithmic calculations herein to avoid erroneous results. Regions lower than this threshold range may be considered to be sufficiently bare soils from which accurate measurements and calculated results may be taken.

The addition of soil contaminants as a result of biosolid application tends to be concentrated in surface soil samples (Mantovi et al., 2005; Bergkvist et al., 2003; Udom et al., 2004; Nyamangara and Mzezewa, 1999).

However, there remains a need for improved methods of remote determination of soil nutrients that offer reduced expense, time savings and availability of mapping soil contamination over large areas.

SUMMARY OF THE INVENTION

The present invention employs remote sensing technology to determine the chemical contents of soils, especially bare soils. The present invention includes methods and systems for remote sensing to map chemical variability in soils, especially bare soils.

The present invention allows one to detect and determine nutrients from reflected light. The invention may be used advantageously for any purpose, such as (1) to determine changes in elemental concentrations of soils amended with biosolids; and (2) to use satellite data, such as LANDSAT TM data (and/or similar satellite or remotely obtained, reluctance data), to map these elemental concentrations of the soils when they are not substantially covered by vegetation ("bare"). It will be understood that the present invention may be applied to any surface, such as any planetary surface.

In general terms, the present invention includes a method of determining the presence of soil nutrients (or soil nutrients in soil) as well as a measurement method followed by transmission of data to a remote processing site. The invention also includes sensing, transmitting and/or reporting systems adapted to determine the presence of soil nutrients through remote sensing.

The Methods

The invention includes a method of determining the presence of soil nutrients (or soil nutrients in soil) from light reflected therefrom. The method comprises the steps of: (a) obtaining a measurement of reflected light from the soil, the measurement comprising a measurement of the respective amount of light in at least two, preferably four wavelength ranges; and (b) relating the approximate amount of the soil nutrient to the respective amounts of light by applying an algorithm using a processor relating the respective amounts of light in the at least two, and preferably four wavelength ranges to the amount of soil nutrients or soil nutrients in the soil.

The processor may be a microprocessor having programming instructions for applying the algorithm.

It is preferred that the algorithm comprises a linear relationship between the approximate amount of the soil nutrient in the soil and sum of (a) the ratio of the amount of light in the first wavelength range to the amount of light in the second wavelength range and (b) the ratio of the amount of light in the third wavelength range to the amount of light in the fourth wavelength range. Typically, wavelength ranges may also include single wavelengths, so it will be understood that reference to wavelength ranges herein also include single wavelengths.

The wavelength ranges typically will be discreet ranges for most detectors, such as satellites, although amounts of light in overlapping ranges may be used as well.

It is preferred that the values of the reflectance are determined as dark object subtracted values as DOS-corrected digital number (DN) values of the selected spectral bands (i.e., wavelength ranges), such as in the case of satellite spectral bands.

The substances detected and determined herein may also be found whether they are considered nutrients or contaminants.

For instance, algorithms based on spectral ratios of LANDSAT TM bands 1, 3, 5 and 7 have been developed and correlated with the actual concentrations of phosphorus, copper and sulfur in soil samples collected from 70 locations across two fields within 24 hours prior to LANDSAT overpass.

It will be understood that reference to the concentrations of phosphorus, copper and sulfur in soil samples means the detection of these elements and/or each of them in whatever oxidation state or other bound state they may be present in the target soil or other substantially bare substrate (such as in natural or unnatural alluvia, as in the case of watershed run-out or man-made spills or other deposits, such as those that may be environmentally damaging.

Typically, the vast majority of phosphorus, sulfur and copper in soil samples will be present in the form of phosphates, sulfates and cupric salts, respectively.

The reflectance of the light in each wavelength region varies with the presence of elemental phosphorus, sulfur and copper, such that the total concentration of phosphorus, copper and sulfur in soil samples may be determined in accordance with the present invention.

Preferably, the measurement of the amount of light in the at least four wavelength ranges comprises the measurement, respectively, of: (i) LANDSAT Thematic Mapper ("TM") band 1, (ii) LANDSAT TM band 3, (iii) LANDSAT TM band 5 and (iv) LANDSAT TM band 7.

Preferred examples of these algorithms are as follows:

$$P(mg/kg) = 4156 - 1690(R51) + 2257(R73);$$

$$Cu(mg/kg) = 75 - 17.9(R51) + 21.9(R73);$$

$$S(mg/kg) = 507 - 14.7(R51) + 214(R73),$$

wherein R51 and R73 are the reflectance measurements, preferably dark-object subtracted (haze corrected) values, of TM band 5 divided by TM band 1 and TM band 7 divided by TM band 3, respectively.

It will be understood that the method and system of the present invention may be used for the determination/estimation of any or all of the soil nutrients phosphorus, copper and/or sulfur in soil samples by using algorithms to relate their amounts to the reflected light, such as described herein.

The present invention therefore includes a method for determining the presence of soil nutrients or soil nutrients in soil from light reflected therefrom, the device comprising (a) a measurement device adapted to measure reflected light from the soil, the measurement comprising a measurement of the respective amount of light in at least four wavelength ranges: (i) from about 0.45 µm to about 0.52 µm; (ii) from about 0.63 µm to about 0.69 µm; (iii) from about 1.55 µm to about 1.75 µm; and (iv) from about 2.08 µm to about 2.35 µm; and (b) a processor at the remote site and capable of relating the approximate amount of the nutrient in the soil to the respective amounts of light by applying an algorithm using a microprocessor relating the respective amounts of light in the at least four wavelength ranges to the amount of soil nutrients or soil nutrients in the soil.

These algorithms can provide output of soil nutrient concentrations (e.g. P, Cu and/or S) of bare soils in mg/kg (the same as ppm) when applied to LANDSAT TM imagery, which passes overhead every 16 days. There are at least three different uses for the present invention: (1) mapping the nutrient concentrations in the soils of watersheds and drainage basins of rivers and tributaries; (2) providing farmers with soil nutrient concentrations of their agricultural fields; and (3) monitoring the environmental disasters involving the spill of toxic chemical contaminants.

This may be expressed in milligrams per kilogram, parts per million or otherwise through appropriate adjustment of the magnitude and dimensions of the algorithms described herein or generated by the present method. It will be understood that the expression of the amount of soil nutrient in terms of milligrams per kilogram, parts per million are only two of several ways to express the amount, and that reference to mathematical equivalents refers to any mathematically or logically related algorithms or expressions.

The method according to the present invention is such that the calculated value of soil nutrients correlates to the actual measured amount of the soil nutrients (based upon well-known physical sampling techniques) by an adjusted square correlation value (i.e., $R^2$ adjusted) in excess of 45% and as high as in excess of 65%.

Method of Detecting Phosphorus in Soil from Reflected Light

With respect to phosphorus, the methods of the present invention include a method of measuring phosphorus in soil from light reflected therefrom, the method comprising the steps of: (a) obtaining a measurement of reflected light from the soil using a light measurement device, the measurement comprising a measurement of the respective amount of light in at least two wavelength ranges; and (b) relating the approximate amount of phosphorus in the soil to the respective amounts of light by applying an algorithm using a microprocessor to relate the respective amounts of light in the at least two wavelength ranges to the amount of phosphorus in the soil.

It is preferred that the algorithm comprises a ratio of the respective amount of light in the at least two wavelength ranges.

It is more preferred that the measurement comprises a measurement of the respective amount of light in at least four wavelength ranges, and most preferably that the algorithm comprises a ratio of the respective amount of light in a first pair of the four wavelength ranges, and a ratio of the respective amount of light in a second pair of the four wavelength ranges.

With respect to phosphorus, the methods of the present invention include a preferred method of measuring phosphorus in soil from light reflected therefrom, the method comprising the steps of: (a) obtaining a measurement of reflected light from the soil, the measurement comprising a measurement of the respective amount of light in at least four wavelength ranges: (i) from about 0.45 μm to about 0.52 μm; (ii) from about 0.63 μm to about 0.69 μm; (iii) from about 1.55 μm to about 1.75 μm; and (iv) from about 2.08 μm to about 2.35 μm from about 2.08 μm to about 2.35 μm; and (b) relating the approximate amount of phosphorus in the soil to the respective amounts of light by applying an algorithm using a microprocessor relating the respective amounts of light in the at least four wavelength ranges to the amount of phosphorus in the soil.

As used herein, reference to mathematical equivalents as applied to algorithms means any algorithm that achieves substantially the same mathematical result from which the concentration of the target substance may be derived. Mathematical equivalents thus may also include those that vary from those disclosed herein in terms of the coefficients used, with the natural and expected variance in accuracy, which may be tolerated in some applications.

The measurement of the amount of light in the at least four wavelength ranges comprises the measurement, respectively, of: (i) LANDSAT TM band 1, (ii) LANDSAT TM band 3, (iii) LANDSAT TM band 5 and (iv) LANDSAT TM band 7. It is preferred that, where the nutrient is phosphorus, the algorithm is selected from the group consisting of $P$ (mg/kg)=$K_1 - K_2$ (R51)+$K_3$ (R73) and mathematical equivalents thereof. In that algorithm, it is preferred that:

P is the amount of phosphorus expressed in milligrams per kilogram;
$K_1$ is a value in the range of from about 4000 to about 4300;
$K_2$ is a value in the range of from about 1600 to about 1780;
$K_3$ is a value in the range of from about 2150 to about 2350;
R51 is a ratio of the amount of reflected light in LANDSAT TM band 5 to the amount of reflected light in LANDSAT TM band 1; and
R73 is a ratio of the amount of reflected light in LANDSAT TM band 7 to the amount of reflected light in LANDSAT TM band 3 and more preferably that:
P is the amount of phosphorus expressed in milligrams per kilogram;
$K_1$ is a value in the range of from about 4100 to about 4200;
$K_2$ is a value in the range of from about 1650 to about 1700;
$K_3$ is a value in the range of from about 2200 to about 2300;
R51 is a ratio of the amount of reflected light in LANDSAT TM band 5 to the amount of reflected light in LANDSAT TM band 1; and
R73 is a ratio of the amount of reflected light in LANDSAT TM band 7 to the amount of reflected light in LANDSAT TM band 3.

The most preferred values are;
P is the amount of phosphorus expressed in milligrams per kilogram;
$K_1$ is a value of about 4156±3;
$K_2$ is a value of about 1690±3;
$K_3$ is a value of about 2257±3;
R51 is a ratio of the amount of reflected light in LANDSAT TM band 5 to the amount of reflected light in LANDSAT TM band 1; and
R73 is a ratio of the amount of reflected light in LANDSAT TM band 7 to the amount of reflected light in LANDSAT TM band 3.

Method of Detecting Copper in Soil from Reflected Light

With respect to copper, the methods of the present invention include a method of measuring copper in soil from light reflected therefrom, the method comprising the steps of: (a) obtaining a measurement of reflected light from the soil using a light measurement device, the measurement comprising a measurement of the respective amount of light in at least two wavelength ranges; and (b) relating the approximate amount of copper in the soil to the respective amounts of light by applying an algorithm using a microprocessor to relate the respective amounts of light in the at least two wavelength ranges to the amount of copper in the soil.

It is preferred that the algorithm comprises a ratio of the respective amount of light in the at least two wavelength ranges.

It is more preferred that the measurement comprises a measurement of the respective amount of light in at least four wavelength ranges, and most preferably that the algorithm comprises a ratio of the respective amount of light in a first pair of the four wavelength ranges, and a ratio of the respective amount of light in a second pair of the four wavelength ranges.

With respect to copper, the methods of the present invention include a preferred method of measuring copper in soil from light reflected therefrom, the method comprising the steps of: (a) obtaining a measurement of reflected light from the soil, the measurement comprising a measurement of the respective amount of light in at least four wavelength ranges: (i) from about 0.45 μm to about 0.52 μm; (ii) from about 0.63 μm to about 0.69 μm; (iii) from about 1.55 μm to about 1.75 μm; and (iv) from about 2.08 μm to about 2.35 μm; and (b) relating the approximate amount of copper in the soil to the respective amounts of light by applying an algorithm using a microprocessor relating the respective amounts of light in the at least four wavelength ranges to the amount of copper in the soil.

The measurement of the amount of light in the at least four wavelength ranges comprises the measurement, respectively, of: (i) LANDSAT TM band 1, (ii) LANDSAT TM band 3, (iii) LANDSAT TM band 5 and (iv) LANDSAT TM band 7.

It is preferred that, where the nutrient is copper, the algorithm is selected from the group consisting of Cu (mg/kg)= $K_1 - K_2$ (R51)+$K_3$ (R73) and mathematical equivalents thereof, wherein:

Cu is the amount of copper expressed in milligrams per kilogram;
$K_1$ is a value in the range of from about 60 to about 90;
$K_2$ is a value in the range of from about 16 to about 20;
$K_3$ is a value in the range of from about 20 to about 24;
R51 is a ratio of the amount of reflected light in LANDSAT TM band 5 to the amount of reflected light in LANDSAT TM band 1; and
R73 is a ratio of the amount of reflected light in LANDSAT TM band 7 to the amount of reflected light in LANDSAT TM band 3, and preferably wherein:
Cu is the amount of copper expressed in milligrams per kilogram;
$K_1$ is a value in the range of from about 70 to about 80;
$K_2$ is a value in the range of from about 17 to about 19;
$K_3$ is a value in the range of from about 21 to about 23;
R51 is a ratio of the amount of reflected light in LANDSAT TM band 5 to the amount of reflected light in LANDSAT TM band 1; and
R73 is a ratio of the amount of reflected light in LANDSAT TM band 7 to the amount of reflected light in LANDSAT TM band 3.

In this algorithm, it is most preferred that:
Cu is the amount of copper expressed in milligrams per kilogram;
$K_1$ is a value of about 75±3;
$K_2$ is a value of about 17.9±3;
$K_3$ is a value of about 21.9±3;
R51 is a ratio of the amount of reflected light in LANDSAT TM band 5 to the amount of reflected light in LANDSAT TM band 1; and
R73 is a ratio of the amount of reflected light in LANDSAT TM band 7 to the amount of reflected light in LANDSAT TM band 3.

Method of Detecting Sulfur in Soil from Reflected Light

With respect to sulfur, the methods of the present invention include a method of measuring sulfur in soil from light reflected therefrom, the method comprising the steps of: (a) obtaining a measurement of reflected light from the soil using a light measurement device, the measurement comprising a measurement of the respective amount of light in at least two wavelength ranges; and (b) relating the approximate amount of sulfur in the soil to the respective amounts of light by applying an algorithm using a microprocessor to relate the respective amounts of light in the at least two wavelength ranges to the amount of sulfur in the soil.

It is preferred that the algorithm comprises a ratio of the respective amount of light in the at least two wavelength ranges.

It is more preferred that the measurement comprises a measurement of the respective amount of light in at least four wavelength ranges, and most preferably that the algorithm comprises a ratio of the respective amount of light in a first pair of the four wavelength ranges, and a ratio of the respective amount of light in a second pair of the four wavelength ranges.

With respect to sulfur, the methods of the present invention include a preferred method of measuring sulfur in soil from light reflected therefrom, the method comprising the steps of: (a) obtaining a measurement of reflected light from the soil, the measurement comprising a measurement of the respective amount of light in at least four wavelength ranges: (i) from about 0.45 µm to about 0.52 µm; (ii) from about 0.63 µm to about 0.69 µm; (iii) from about 1.55 µm to about 1.75 µm; and (iv) from about 2.08 µm to about 2.35 µm; and (b) relating the approximate amount of sulfur in the soil to the respective amounts of light by applying an algorithm using a microprocessor relating the respective amounts of light in the at least four wavelength ranges to the amount of sulfur in the soil.

The measurement of the amount of light in the at least four wavelength ranges comprises the measurement, respectively of: (i) LANDSAT TM band 1, (ii) LANDSAT TM band 3, (iii) LANDSAT TM band 5 and (iv) LANDSAT TM band 7.

It is preferred that, where the nutrient is sulfur, the algorithm is selected from the group consisting of S (mg/kg)=$K_1$−$K_2$ (R51)+$K_3$ (R73) and mathematical equivalents thereof, wherein:

S is the amount of sulfur expressed in milligrams per kilogram;
$K_1$ is a value in the range of from about 450 to about 550;
$K_2$ is a value in the range of from about 13 to about 17;
$K_3$ is a value in the range of from about 210 to about 220;
R51 is a ratio of the amount of reflected light in LANDSAT TM band 5 to the amount of reflected light in LANDSAT TM band 1; and
R73 is a ratio of the amount of reflected light in LANDSAT TM band 7 to the amount of reflected light in LANDSAT TM band 3;

and preferably wherein:
S is the amount of sulfur expressed in milligrams per kilogram;
$K_1$ is a value in the range of from about 480 to about 530;
$K_2$ is a value in the range of from about 14 to about 16;
$K_3$ is a value in the range of from about 212 to about 216;
R51 is a ratio of the amount of reflected light in LANDSAT TM band 5 to the amount of reflected light in LANDSAT TM band 1; and
R73 is a ratio of the amount of reflected light in LANDSAT TM band 7 to the amount of reflected light in LANDSAT TM band 3.

In this algorithm, it is most preferred that:
S is the amount of sulfur expressed in milligrams per kilogram;
$K_1$ is a value of about 507±3;
$K_2$ is a value of about 14.7±3;
$K_3$ is a value of about 214±3;
R51 is a ratio of the amount of reflected light in LANDSAT TM band 5 to the amount of reflected light in LANDSAT TM band 1; and
R73 is a ratio of the amount of reflected light in LANDSAT TM band 7 to the amount of reflected light in LANDSAT TM band 3.

The present invention in all its embodiments may additionally comprise the step of generating a report of the approximate amount of the nutrient species in the soil. This may be done using electronics adapted to digitize and process the data using an appropriate algorithm, such as that described herein. For instance, the report may include an estimate of the amount of the nutrient(s) per kilogram of soil.

The method of the present invention in all its embodiments may also include the step of transmitting data relating to the approximate amount of the nutrient(s) in the soil to a site remote from the site where the measurement takes place. This may be done using any transmission method including land line or wireless transmission.

The method of the present invention in all its embodiments may additionally include a display of an image representing the data generated by the system, so as to be able to visualize the results of the assay method carried out by the system, in accordance with the present invention.

This method may also be used advantageously where the reflected light is sensed remotely by aircraft, satellite, vehicle (such as typically, a motorized piece of farming equipment or the like), or from a pole, building or other fixed support. For instance, the measurement device may include sensors adapted to measure the same spectral bands on a tractor or other farming vehicle, such as for measuring the phosphorus, sulfur and/or copper in the bare soil, such as by being mounted in front and/or in back of the tractor.

Processing of the data may take place at the site of light uptake or may be carried out at a remote location after transmission of the raw data. The estimated report may be sent to farmers, businesses, agricultural reporting stations, farm bureaus and cooperative offices, or to public authorities, to advise or warn of the level of soil nutrients or soil contaminants, especially where those levels are outside desired levels, or otherwise at elevated, deficient or dangerous levels.

The method of the present invention may further include taking some remediation action or other action to alter the soil nutrients or soil contaminants, which may be any logical action consistent with environmental and/or agricultural practices, such as through the washing or irrigation of soils, application of fertilizer or other soil amendment, or excavation of soils to remove contaminants, etc.

The Systems

The invention also includes a system for determining the presence of soil nutrients or soil nutrients in soil from light reflected therefrom, the system comprising: (a) a measurement device adapted to measure reflected light from the soil, the measurement comprising a measurement of the respective amount of light in at least four wavelength ranges, preferably such as those set forth above, and (b) a processor capable of relating the approximate amount of the nutrient(s) in the soil to the respective amounts of light by applying an algorithm using a microprocessor relating the respective amounts of light in the at least four wavelength ranges to the amount of soil nutrients or soil nutrients in the soil.

The invention also includes a system for determining the presence of soil nutrients or soil nutrients in soil from light reflected therefrom, the system comprising: (a) electronic means adapted to measure reflected light from the soil, the measurement comprising a measurement of the respective amount of light in at least four wavelength ranges, preferably such as those set forth above, and (b) electronic means capable of relating the approximate amount of the nutrient(s) in the soil to the respective amounts of light by applying an algorithm using a microprocessor relating the respective amounts of light in the at least four wavelength ranges to the amount of soil nutrients or soil nutrients in the soil.

System for Detecting Phosphorus in Soil from Reflected Light

For phosphorus, the system of the present invention may be understood as a system for measuring phosphorus in soil from light reflected therefrom, the device comprising: (a) a measurement device adapted to measure reflected light from the soil, the measurement comprising a measurement of the respective amount of light in at least four wavelength ranges: (i) from about 0.45 µm to about 0.52 µm; (ii) from about 0.63 µm to about 0.69 µm; (iii) from about 1.55 µm to about 1.75 µm; and (iv) from about 2.08 µm to about 2.35 µm; and (b) a processor capable of relating the approximate amount of the phosphorus in the soil to the respective amounts of light by applying an algorithm using a microprocessor relating the respective amounts of light in the at least four wavelength ranges to the amount of phosphorus in the soil.

The measurement of the amount of light in the at least four wavelength ranges comprises the measurement, respectively, of: (i) LANDSAT TM band 1, (ii) LANDSAT TM band 3, (iii) LANDSAT TM band 5 and (iv) LANDSAT TM band 7.

Where the nutrient is phosphorus, the algorithm may be selected from the group consisting of P (mg/kg)=$K_1-K_2$(R51)+$K_3$(R73) and mathematical equivalents thereof. It is in such algorithm that:

P is the amount of phosphorus expressed in milligrams per kilogram;

$K_1$ is a value in the range of from about 4100 to about 4200;

$K_2$ is a value in the range of from about 1650 to about 1700;

$K_3$ is a value in the range of from about 2200 to about 2300;

R51 is a ratio of the amount of reflected light in LANDSAT TM band 5 to the amount of reflected light in LANDSAT TM band 1; and R73 is a ratio of the amount of reflected light in LANDSAT TM band 7 to the amount of reflected light in LANDSAT TM band 3.

and most preferably that:

P is the amount of phosphorus expressed in milligrams per kilogram;

$K_1$ is a value of about 4156±3;

$K_2$ is a value of about 1690±3;

$K_3$ is a value of about 2257±3;

R51 is a ratio of the amount of reflected light in LANDSAT TM band 5 to the amount of reflected light in LANDSAT TM band 1; and R73 is a ratio of the amount of reflected light in LANDSAT TM band 7 to the amount of reflected light in LANDSAT TM band 3.

The measurement device and processor may be incorporated into the same article or vehicle, or may be distributed between different components of the system.

The processor may be of any type appropriate to carry out the calculation and determination/estimation of the amount of the target substance as described herein. It may be in data communicative contact with the measurement device through any appropriate means, such as through the use of data transmission means and/or storage media known and used in the information technology and data processing fields.

The measurement device may be selected from the group consisting of cameras, photosensors and satellites.

The system of the present invention may additionally include a report generator adapted to generate a report of the approximate amount of the nutrient(s) in the soil. Such a report generator may be any device that is adapted to place the data into a tangible medium, such as a printer, CD burner, flash memory, magnetic storage media, etc.

The system of the present invention may additionally include a display for displaying an image representing the data generated by the system, so as to be able to visualize the results of the assay method carried out by the system, in accordance with the present invention. Typical digital images for use in this method may be prepared from digital information taken from aerial platforms or satellites, and either may be stored digitally when taken or transferred into digital format. Typical sources of data from digital images may include digital or film cameras or spectrometers carried by aircraft or satellite.

The system may additionally include a transmitter adapted to transmit data relating to the approximate amount of the nutrients in the soil from the processor to a site remote from the site where the measurement takes place. Such a transmitter may include those adapted to send data such as through land line or wireless transmission, including telephone, internet, cell phone, radio and the like.

The measurement device may be any device adapted to sense and record and/or transmit the light frequencies described above. Examples include photosensors or any appropriate type considering the distances, reflectivity profile, dispersion, and reflectance in each application of the invention, cameras, digital cameras and video cameras, etc.

The processor may be any data processing device having programming instructions for applying the algorithm(s), such as preferably a microprocessor.

It is preferred that the algorithm comprises a linear relationship between the approximate amount of the nutrient(s) in the soil and sum of (a) the ratio of the first wavelength to the second wavelength and (b) the ratio of the third wavelength to the fourth wavelength.

The measurement device may be placed in any position from which it can sense the required light frequencies, such as on an aircraft or satellite or on a support, such as a dedicated tower structure, such as a barn or silo. The measurement device may also be in the form of a handheld device, such as a camera connected to a processor for processing the recorded light frequencies, the device may also be in the form of a device similar to a personal digital assistant with light recording and processing functions. For instance, the measurement device may include sensors adapted to measure the same spectral bands on a tractor or other farming vehicle, such as for measuring the phosphorus, sulfur and/or copper in the bare soil, such as by being mounted in front and/or in back of the tractor.

Another variation of the invention is a system using transmission of light measurement data to processor at a different location, recognizing that the processing may be done at a different location than the light sensing/recording.

In general terms, this variation is a system for determining the presence of soil nutrients or soil nutrients in soil from light reflected therefrom, the device comprising (a) a measurement device adapted to measure reflected light from the soil, the measurement comprising a measurement of the respective amount of light in at least four wavelength ranges: (i) from about 0.45 µm to about 0.52 µm; (ii) from about 0.63 µm to about 0.69 µm; (iii) from about 1.55 µm to about 1.75 µm; and (iv) from about 2.08 µm to about 2.35 µm; and (b) a processor at the remote site and capable of relating the approximate amount of the nutrient in the soil to the respective amounts of light by applying an algorithm using a microprocessor relating the respective amounts of light in the at least four wavelength ranges to the amount of the soil nutrients in the soil.

Method of Developing Algorithms, Processors and Systems for Other Wavelengths and/or Detectors The invention also includes a method of developing a system for determining the presence of soil nutrients or soil nutrients in soil from light reflected therefrom, the device comprising (a) obtaining a measurement of reflected light from the soil, the measurement comprising a measurement of the respective amount of light of at least two wavelengths or wavelength ranges; (b) developing an algorithm relating the respective amounts of light in the at least two wavelengths or wavelength ranges to the amount of soil nutrients or soil nutrients in the soil through linear regression analysis; (c) producing a processor capable of relating the approximate amount of the nutrient in the soil to the respective amounts of light by applying an algorithm relating the respective amounts of light in the at least four wavelength ranges to the amount of soil nutrients or soil nutrients in the soil; and (d) providing a measurement device adapted to measure reflected light from the soil and adapted to provide data relating to the measurement to the processor.

It is preferred that the method include using a ratio of the respective amount of light in each of the at least two wavelengths or wavelength ranges.

It is preferred that the at least two wavelengths or wavelength ranges be in the visible range (typically wavelengths from about 380 to 750 nm; about between 0.380 and 0.750 micrometers) and/or the infrared range (typically a wavelength between 0.7 and 300 micrometers).

It is more preferred that the method use a measurement of reflected light from the soil, the measurement comprising a measurement of the respective amount of light in at least four wavelengths or wavelength ranges.

It is also preferred that the algorithm comprises a ratio of the respective amount of light in said at least two wavelength ranges, and most preferably that the algorithm comprises a ratio of the respective amount of light in a first pair of the four wavelength ranges, and a ratio of the respective amount of light in a second pair of the four wavelength ranges.

The invention also includes a method of developing a system for determining the presence of soil nutrients or soil nutrients in soil from light reflected therefrom, the device comprising (a) obtaining a measurement of reflected light from the soil, the measurement comprising a measurement of the respective amount of light of at least two wavelengths; (b) developing an algorithm relating the respective amounts of light in the at least two wavelengths to the amount of soil nutrients or soil nutrients in the soil through linear regression analysis; (c) producing a processor capable of relating the approximate amount of the nutrient in the soil to the respective amounts of light by applying an algorithm relating the respective amounts of light in the at least four wavelength ranges to the amount of soil nutrients or soil nutrients in the soil; and (d) providing a measurement device adapted to measure reflected light from the soil and adapted to provide data relating to the measurement to the processor.

The present invention may be extended to other wavelength bands that may be obtained from other detectors or multiple detectors, such as alternative satellites (or from more than one satellite), such as, for instance, the Digital Globe World Watch II satellite, which may offer different reflectance bands, and may offer greater resolution than LANDSAT TM. The method of the present invention may be practiced with any suitable detector from any desired or practical distance, from only a few feet as in the case of a vehicle-mounted detector, to typical tower height, to typical aircraft altitudes, to outer space.

Accordingly, the preferred embodiment of the present invention allows the operator, for instance, (1) to determine changes in chemical concentrations of soils that are amended with treated sewage sludge or recently treated with fertilizer (which may be compared to recorded fertilizer placement, for agricultural purposes); and 2) to determine if LANDSAT TM data can be used to map surface chemical characteristics of such amended soils. For this embodiment, two fields in NW Ohio were selected, designated as F34 and F11 that had been applied with 34 and 11 ton acre$^{-1}$ of biosolids, respectively. Soil samples from a total of 70 sampling locations across the two fields were collected one day prior to LANDSAT 5 overpass and were analyzed for several elemental concentrations. The accumulation of Ba, Cd, Cu, S and P were found to be significantly higher in the surface soils of field F34, compared to field F11. Regression equations were established to search for algorithms that could map these five elemental concentrations in the surface soils using six, dark-object subtracted (DOS) LANDSAT TM bands and the 15 non-reciprocal spectral ratios derived from these six bands for the May 20, 2005, LANDSAT 5 TM image. Phosphorus (P) had the highest $R^2$ adjusted value (67.9%) among all five elements considered, and the resulting algorithm employed only spectral ratios. This model was successfully tested for robustness by applying it to another LANDSAT TM image obtained on Jun. 5, 2005. The results enabled us to conclude that LANDSAT TM imagery of bare-soil fields can be used to quantify and map the spatial variation of total phosphorus concentration in surface soils. This research has significant implications for identification and mapping of areas with high phosphorus, which is important for implementing and monitoring the best phosphorus management practices across the region.

In addition to the features mentioned above, objects and advantages of the present invention will be readily apparent upon a reading of the following description and through practice of the present invention.

Novel features and advantages of the present invention, in addition to those mentioned above, will become apparent to those skilled in the art from a reading of the following detailed description in conjunction with the accompanying drawings summarized as follows.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF PREFERRED EMBODIMENT(S)

In accordance with the foregoing summary, the following is a detailed description of the preferred embodiments of the invention, which are considered to be the best mode thereof. The preferred method and system herein described is not intended to be exhaustive or to limit the invention to the precise forms disclosed. They are chosen and described to explain the principles of the invention and the application of the method to practical uses so that others skilled in the art may practice the invention.

Figure 1:
FIG. 1 is a LANDSAT 5 TM natural color image (TM bands 1, 2, and 3 displayed as BGR, respectively) obtained on May 20, 2005 showing the eastern part of Lucas County in northwest Ohio; this area drains into Lake Erie, which is towards the northern side (top) of the image, in accordance with one embodiment of the present invention.
Figure 1:
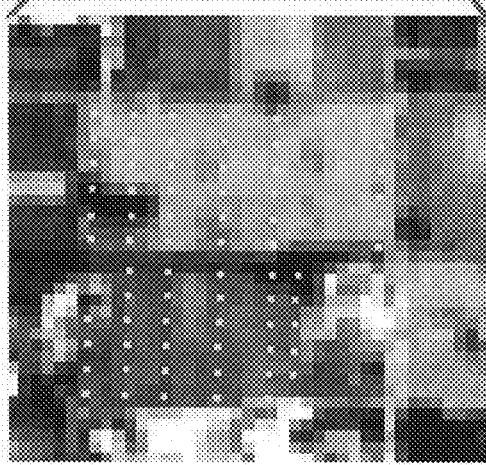

Application to the Remote Determination of Phosphorus
Materials and Methods
Soil Sampling and Chemical Analysis Two adjacent agricultural fields, designated F34 and F11, that received a cumulative amount of 34 ton acre-1 (76 mg hac-1) and 11 ton acre-1 (25 mg hac-1) of Class B biosolids on a dry weight basis during the period of 1985-2002 were selected for this embodiment (See FIG. 1).

FIG. 1 shows the LANDSAT 5 TM natural color image (TM bands 1, 2, and 3 displayed as BGR, respectively) obtained on May 20, 2005 showing the eastern part of Lucas County in northwest Ohio; this area drains into Lake Erie, which is towards the northern side (top) of the image. The fields permitted for Class B biosolid application in the area are outlined in the image. The fields marked with red borders are the experimental fields used in this embodiment. Soil sampling locations of the study area were shown as yellow dots in the insert image.

Soil samples were collected at 0, 30, and 50 cm depths from each of the 70 sampling locations across the two fields. These fields were selected because they are representative of large areas of northwest Ohio where land application of biosolids has become an important agricultural practice.

The soil samples were collected on May 19, 2005, one day prior to LANDSAT over pass, and the sampling locations were marked using a Trimble GeoExplorer (Trimble Navigation Limited, CA, USA) global positioning system (GPS) receiver. The collected soil samples were dried and passed through a 2 mm sieve. The moisture content of the surface soil samples was measured using the gravimetric method. The source of sewage sludge for the agricultural fields in the study area was the Oregon Waste Soil Treatment Plant (OWSTP). The basic composition of the sewage sludge of OWSTP is typical of the bio-solids produced in Ohio, which is regulated within the limits set by the U.S. Environmental Protection Agency (USEPA) under the part 503 rule (USEPA, 2002).

Soil samples (approximately 0.5 g) were digested with concentrated $HNO_3$, according to USEPA method SW846-3051A (USEPA, 1998) using a Mars Xpress microwave digestion unit (CEM, Matthews, N.C., USA). The digested solution was filtered and then analyzed for As, B, Be, Ca, Cd, Cr, Cu, Fe, K, Mg, Mn, Mo, Na, Ni, P, Pb, S, Se, Si and Zn concentrations using inductively coupled plasma-optical emission spectrometry (ICP-OES) (IRIS Intrepid II, Thermo Scientific, Waltham, Mass., USA). Quantification was achieved using matrix matched high and low concentration standards for each element. Internal quality controls and blanks were run every ten samples in order to quantify cross-contamination and recovery efficiencies.

Analysis of variance (ANOVA) was used to compare the accumulation of each element in the F34 and F11 fields using SAS version 9.1 statistical software (SAS Institute Inc., Cary, N.C., USA). An alpha level of 0.05 was used to determine the significance.

LANDSAT Data Acquisition and Analysis

The LANDSAT image frames of May 20 and Jun. 5, 2005, covering the study area were downloaded soon after soil sampling. The images were then processed with the ER Mapper image processing software, a commercial product of Earth Resources Mapping, Inc. The study area was located within the LANDSAT overpass region of Path 20, Row 31. The natural color image of the study area, overlaid with outlines of the fields permitted for Class B biosolid applications, is shown in FIG. 1. The locations of all the 70 soil sampling points collected one day prior to LANDSAT 5 overpass were also shown separately in FIG. 1 on the natural color image of the study area. The study site was dry, without any vegetation, such that the image spectral reflectance represent the spectral reflectance of the bare soil. The procedure for developing the GIS database of the Class B biosolid permitted fields in Wood and Lucas counties of northwest Ohio was reported in detail by McNulty (2005).

Based on the locations of the 70 soil samples, the dark object subtracted (DOS) pixel values corresponding to the LANDSAT TM bands 1-5 and 7 were derived from the original May 20, 2005 image. The spectral range of these LANDSAT TM bands are as follows: band 1: 450-520 nm; band 2: 520-600 nm; band 3: 630-690 nm; band 4: 760-900 nm; band 5: 1550-1750 nm; and band 7: 2080-2350 nm.

The dark object of each spectral band is defined as one value less than the minimum digital number found in all the pixels of the image (Vincent et al., 2004) referenced herein below. The detailed procedure for DOS and its effects on removal of atmospheric haze was given in Vincent (1997) and Vincent et al. (2004) referenced herein below.

From the DOS-corrected digital number (DN) values of the six LANDSAT single bands, 15 non-reciprocal spectral ratios were calculated. These spectral ratios are: R2,1; R3,1; R3,2; R4,1; R4,2; R4,3; R5,1; R5,2; R5,3; R5,4; R7,1; R7,2; R7,3; R7,4; R7,5 where R represents the ratio and the numbers represent the LANDSAT TM band numbers (Vincent, 1997). The spectral ratios were calculated using the MINITAB statistical software (MINITAB Inc., State College, Pa., USA).

LANDSAT TM Best Spectral Ratio Model Development and Validation

The relationships between the chemical concentrations of the surface soil samples and the DOS DN values corresponding to the six single bands and the 15 non-reciprocal spectral ratios were developed by regression analysis. Using the MINITAB regression analysis component the best subsets regression was employed, and only the top two models with the highest R2 adjusted values were chosen to report for each number of variables. The best subsets procedure was used for sequentially entering independent variables one at a time to improve the regression equation's predictive ability. The reported models from the best subset regression output were tested for autocorrelation with a Durbin-Watson (DW) statistical test (Durbin and Watson, 1951). This tests for autocorrelation in the input parameters. Finally, the model which had the highest R2 adjusted and that also passed the DW test was selected as the best model for given inputs. This procedure was reported in detail elsewhere by Vincent (2000) and Vincent et al. (2004). The identified best model was then applied to the same May 20, 2005, LANDSAT image, which was used in developing the model to map the elemental concentration of the surface soils. The model was also applied and validated using the Jun. 5, 2005, LANDSAT image, which was obtained 17 days after the soil sampling. In the LANDSAT images that were applied with the best model, masks were created to limit the display to only bare soil fields.

Laboratory Spectral Data Acquisition and Analysis

A Fieldspec Pro spectroradiometer (ASDInc., Boulder, Colo., USA) with a spectral range of 350-2500 nm was used to obtain the reflectance spectra of the collected soil samples in the laboratory, with a quartz-tungsten-halogen (QTH) lamp as a light source. Diffused light from the 100 W Lowell Pro-Light was used to illuminate the soil samples that were placed in a Petri plate at 45° angles, when spectra were collected in the laboratory. The fore-optics of the spectroradiometer was aligned vertically, and the height of the fore-optics was adjusted so that reflected light only from the surface of the soil samples filled the field of view (FOV) of the instrument. The height of the fore-optics was kept constant throughout the experiment at 20 cm from the surface of each soil sample. The same experimental setup was used to obtain the spectra of all the soil samples collected at 3 different depths from each field.

Calibration spectra of a white Spectralon panel (Labsphere Inc., North Sutton, N.H.) were acquired before recording the soil spectra. The spectral recording software in the spectroradiometer was set in such a way that each reflectance spectrum recorded was obtained by collecting and averaging 20 individual reflectance spectra. Each spectrum was normalized by dividing it by the measured spectrum of the standard (Spectralon panel). The configuration of the ASD spectroradiometer consists of three detectors, each collecting spectra from the 350-1050, 900-1850, and 1700-2500 nm spectral regions, respectively. The spectra collected by these detectors within the instrument are not spliced together. Thus, each normalized spectrum was splice-corrected with the ASD ViewSpec software (ASD Inc., Boulder, Colo.). Individual spectral measurements of the soil samples corresponding to the three sampling depths in each of the fields were then averaged to overcome the spectral variations.

Results

Soil Chemical Concentration

The chemical concentration of the soils at 0, 30 and 50 cm depths and the moisture content of the surface soils in both the F34 and F11 treated fields are shown in Table 1.

TABLE 1

Chemical concentration of soils applied with 34 ton acre$^{-1}$ (F34) and 11 ton acre$^{-1}$ (F11) of Class B Biosolids

| Treatment | Soil Depth (cm) | Ba (mg/kg) | Cd (mg/kg) | Cu (mg/kg) | S (mg/kg) | P (mg/kg) | Moisture (%) |
|---|---|---|---|---|---|---|---|
| F34 | 0 | 161 (±28.5) | 5.7 (±0.5) | 55 (±5) | 405 (±57) | 2550 (±625) | 9.7 (±7.3) |
|  | 30 | 103 (±16.7) | 5.7 (±0.46) | 37 (±5.1) | 197 (±55) | 796 (±439) |  |
|  | 50 | 97 (±14.4) | 5.6 (±1.1) | 35 (±6.1) | 154 (±31) | 557 (±103) |  |
| F11 | 0 | 98 (±19.1) | 3.6 (±1.9) | 37 (±6.6) | 265 (±68) | 988 (±303) | 5.5 (±2.5) |
|  | 30 | 100 (±13.3) | 3.5 (±0.9) | 31 (±5.1) | 165 (±49) | 588 (±177) |  |
|  | 50 | 99 (±13.5) | 3.7 (±0.9) | 31 (±4.9) | 132 (±51) | 558 (±149) |  |

The given values are means ± standard deviation of 35 replicates

Among all the chemicals that were analyzed, the accumulation of Ba, Cd, Cu, S and P were significantly (pb0.05) higher in the surface soils of F34, compared to F11 (Table 1). There was no significant difference in the chemical concentrations at 30 and 50 cm depths among the F34 and F11 soils. Also, the moisture content of the surface soils in both the fields was similar (Table 1). The soils were of the prevalent latty silty clay type with surface soils having 40-55% of clay and 3-5% of organic matter (Soil Survey Staff, 2007).

Spectral Reflectance of Soil Samples

Figure 2:
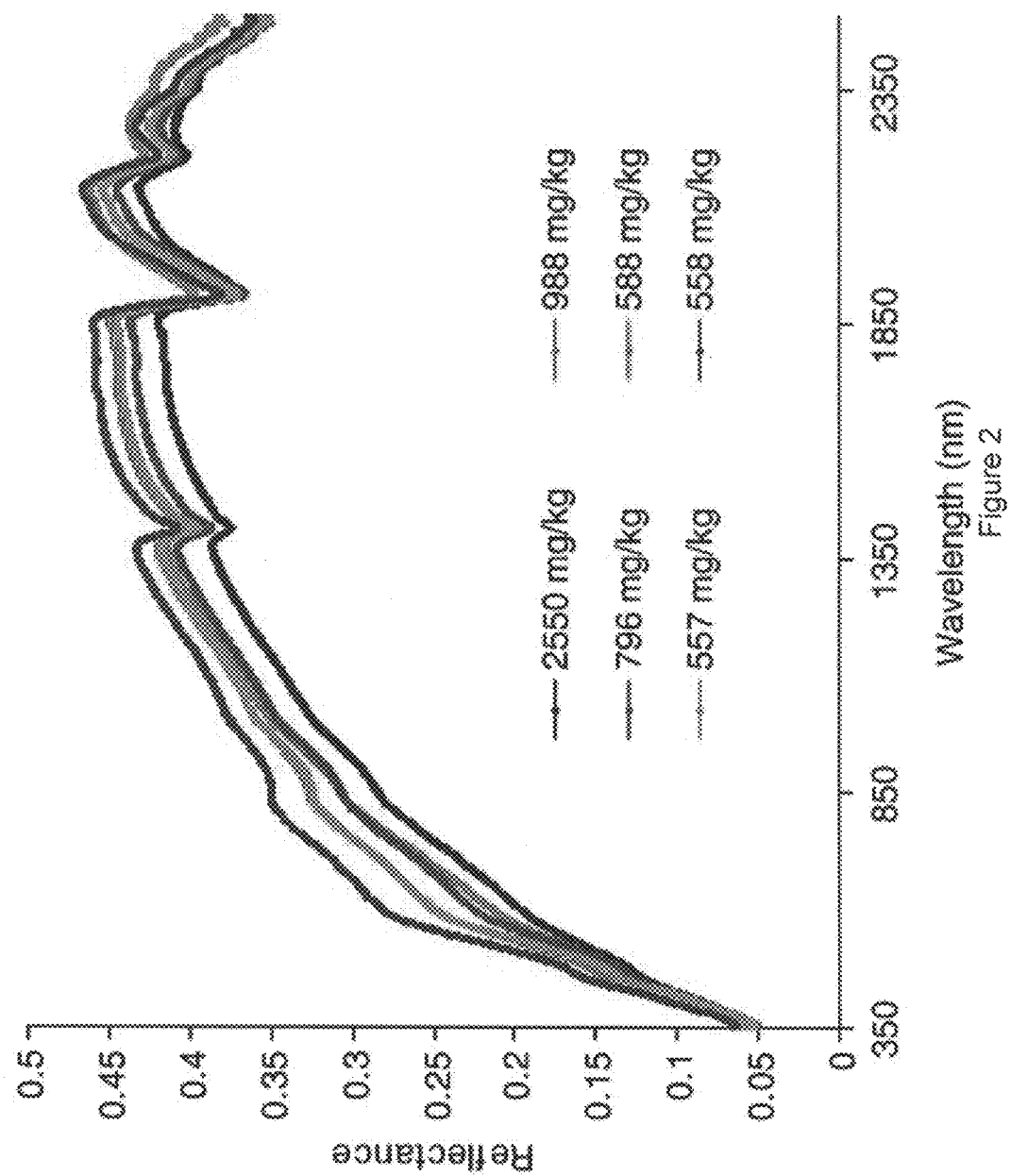
FIG. 2 is a graph showing averaged (n=35) spectral reflectance of the soil samples collected at 0, 30 and 50 cm depths in F34 and F11 treated fields, in accordance with one embodiment of the present invention.

The averaged spectral reflectance of the F34 and F11 soils obtained at 0, 30 and 50 cm depths are shown in FIG. 2. Also given are the averaged total P concentrations (in mg/kg) corresponding to the soil samples. The spectral reflectance of the soils decreases with increase in P concentration. The surface soil samples of field F34 have high P concentration (2550 mg/kg) and low spectral reflectance throughout the spectral range, compared to the rest of the soil samples. The reflectance of the soil samples gradually increases from 350 nm to about 2200 nm, then decreases to about 2500 nm. There is a broad, shallow reflectance minimum between 600 and 1100 nm (centered about 850 nm), which is likely due to trace amounts of iron present in the soils. The two absorption bands (reflectance minima) near 1400 and 1900 nm in the spectra are due to the in-situ soil moisture. All the soil samples that were used in obtaining the spectra in the laboratory were dried and passed through a 2 mm sieve to minimize the effects of soil moisture and particle size on the spectra.

LANDSAT Spectral Ratio Model

Regression equations were established to determine the chemical concentrations of Ba, Cd, Cu, S and P, which are significantly (pb 0.05) higher in the surface soils of F34 compared to F11, using the DOS-corrected six TM bands and the non-reciprocal spectral ratios. The best spectral ratio input models that pass the DW test of significance along with their R2 adjusted and standard error values are given in Table 2.

TABLE 2

Best spectral ration input models for phosphorus, copper, and sulfur that pass the Durbin-Watson test along with the values of $R^2$ adjusted and SE (standard error)

| Chemical | Best spectral ratio model | $R^2$ adjusted (%) | SE (mg/kg) |
| --- | --- | --- | --- |
| Phosphorus | 4156-1690 (R51) + 2257 (R73) | 67.9 | 531.2 |
| Copper | 75-17.9 (R51) + 21.9 (R73) | 59 | 6.9 |
| Sulfur | 507-14.7 (R51) + 214 (R73) | 49.3 | 66.8 |

Note:
The models developed for Cd and Ba did not pass the Durbin-Watson test at 5% level of significance.

Figure 3:
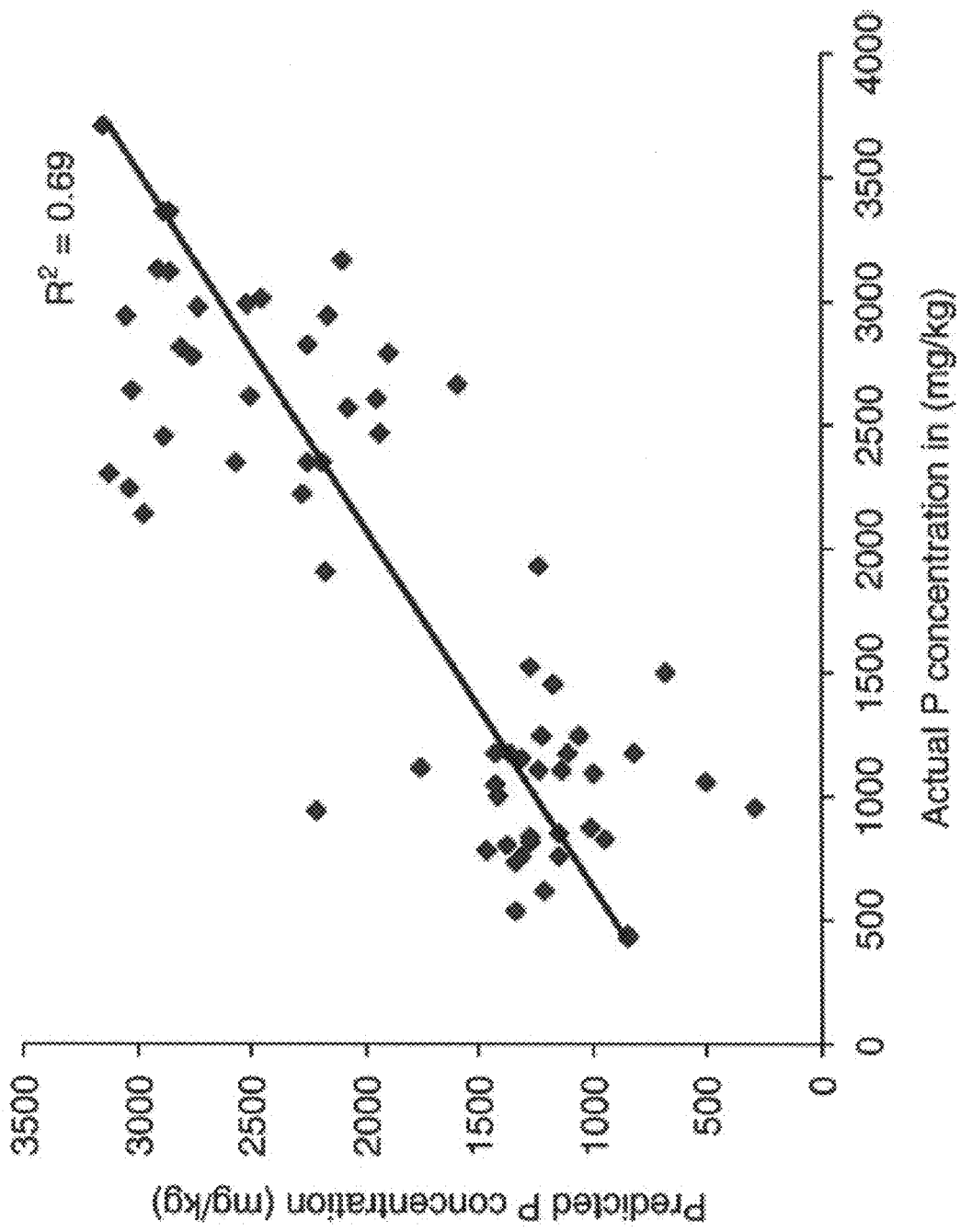
FIG. 3 is a graph showing actual versus predicted phosphorus concentration (in mg/kg) of surface soil samples using the dark object subtracted best phosphorus spectral ratio model being applied to the LANDSAT 5 TM frame of May 20, 2005, which was also used for developing the model, in accordance with one embodiment of the present invention.
Figure 4:
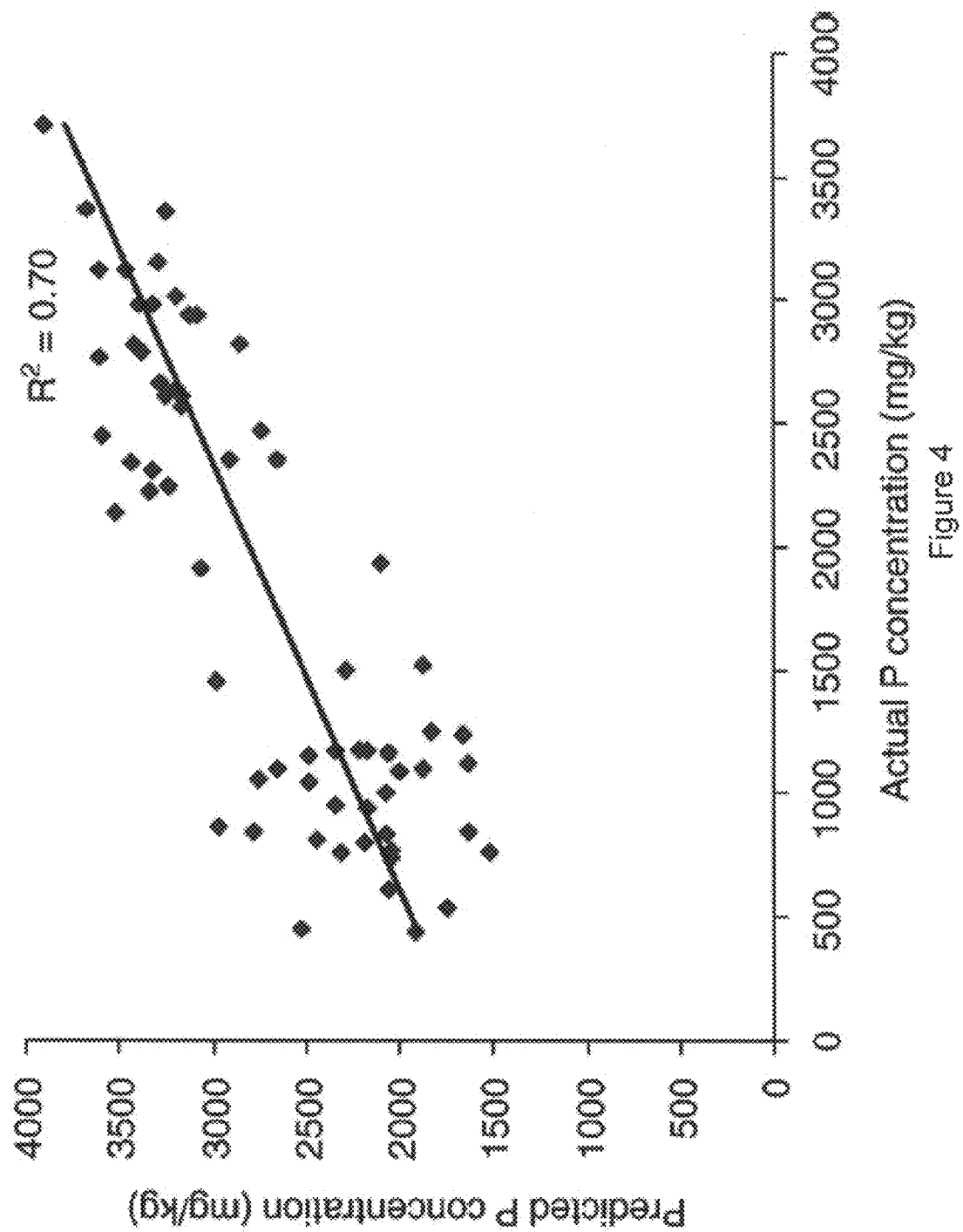
FIG. 4 is a graph showing actual versus predicted phosphorus concentration (in mg/kg) of surface soil samples using the dark object subtracted best phosphorus spectral ratio model being applied to the LANDSAT 5 TM frame of Jun. 5, 2005, in accordance with one embodiment of the present invention.

None of the single band models passed the DW test. Phosphorus had the highest R2 adjusted value (67.9%) among the chemical attributes that passed the DW test (Table 2) and are considered for mapping phosphorus with LANDSAT TM data. Hence, only the phosphorus results were shown in this paper. The phosphorus values obtained from chemical analysis of the 70 surface soil sampling locations versus the predicted values of phosphorus for the same locations obtained by applying the phosphorus spectral ratio model P(mg/kg)= 4156−1690 (R51)+2257 (R73) to the May 20, 2005, LANDSAT TM frame is given in FIG. 3. The phosphorus spectral ratio model was also applied to the Jun. 5, 2005 LANDSAT image frame and the predicted phosphorus values were plotted against the phosphorus values obtained by the soil analysis (FIG. 4). The model performed well in predicting the phosphorus concentrations of surface soil when applied to either of the LANDSAT TM images.

Figure 5:
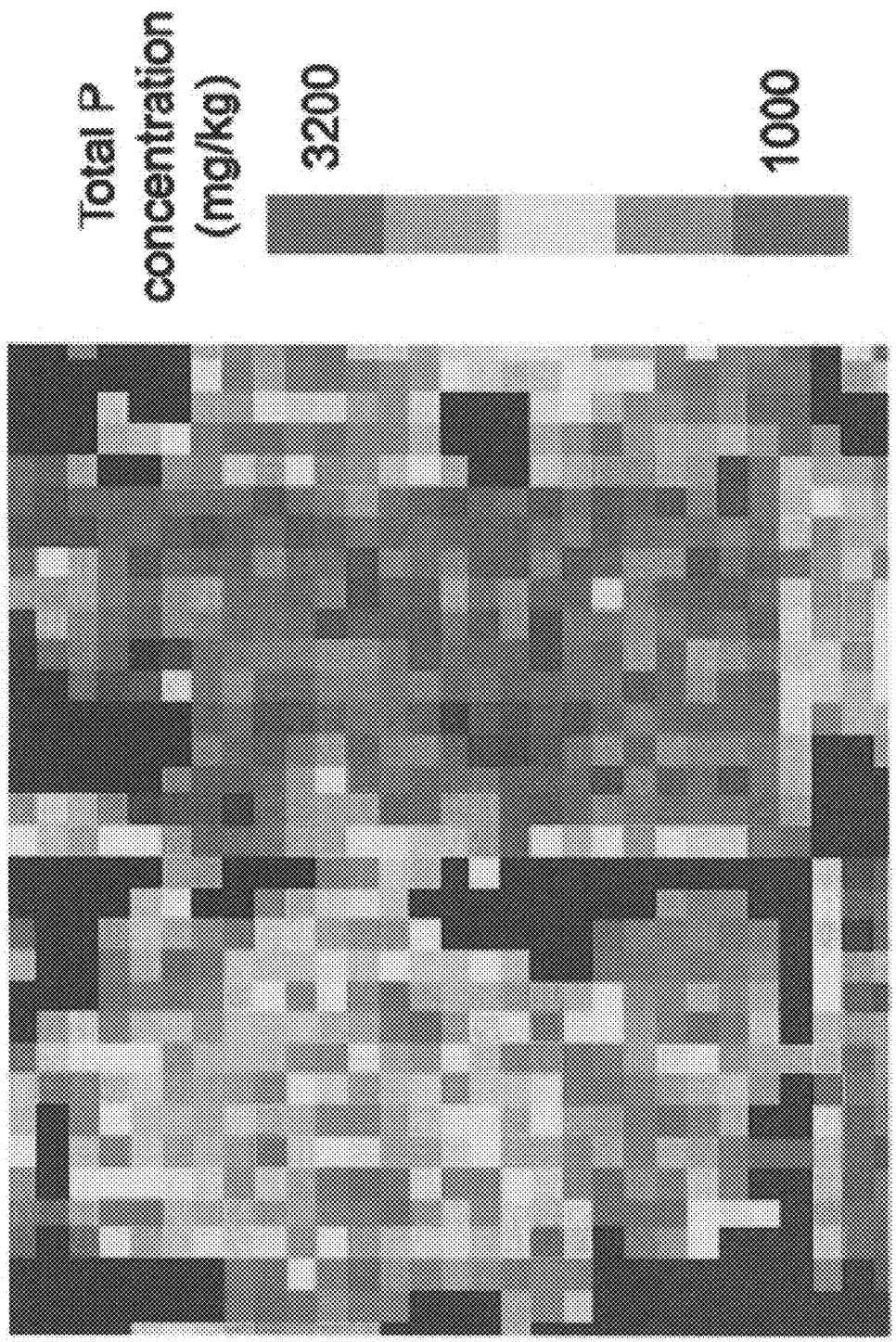
FIG. 5 is an image showing the total phosphorus concentration (mg/kg) in surface soil samples of fields F34 (left side of the image) and F11 (right side of the image), displayed as red (high phosphorus content) to turquoise (low phosphorus content), obtained by applying the best phosphorus spectral ratio model to the LANDSAT 5 TM frame of May 20, 2005 which was also used for developing the model, in accordance with one embodiment of the present invention.
Figure 6:
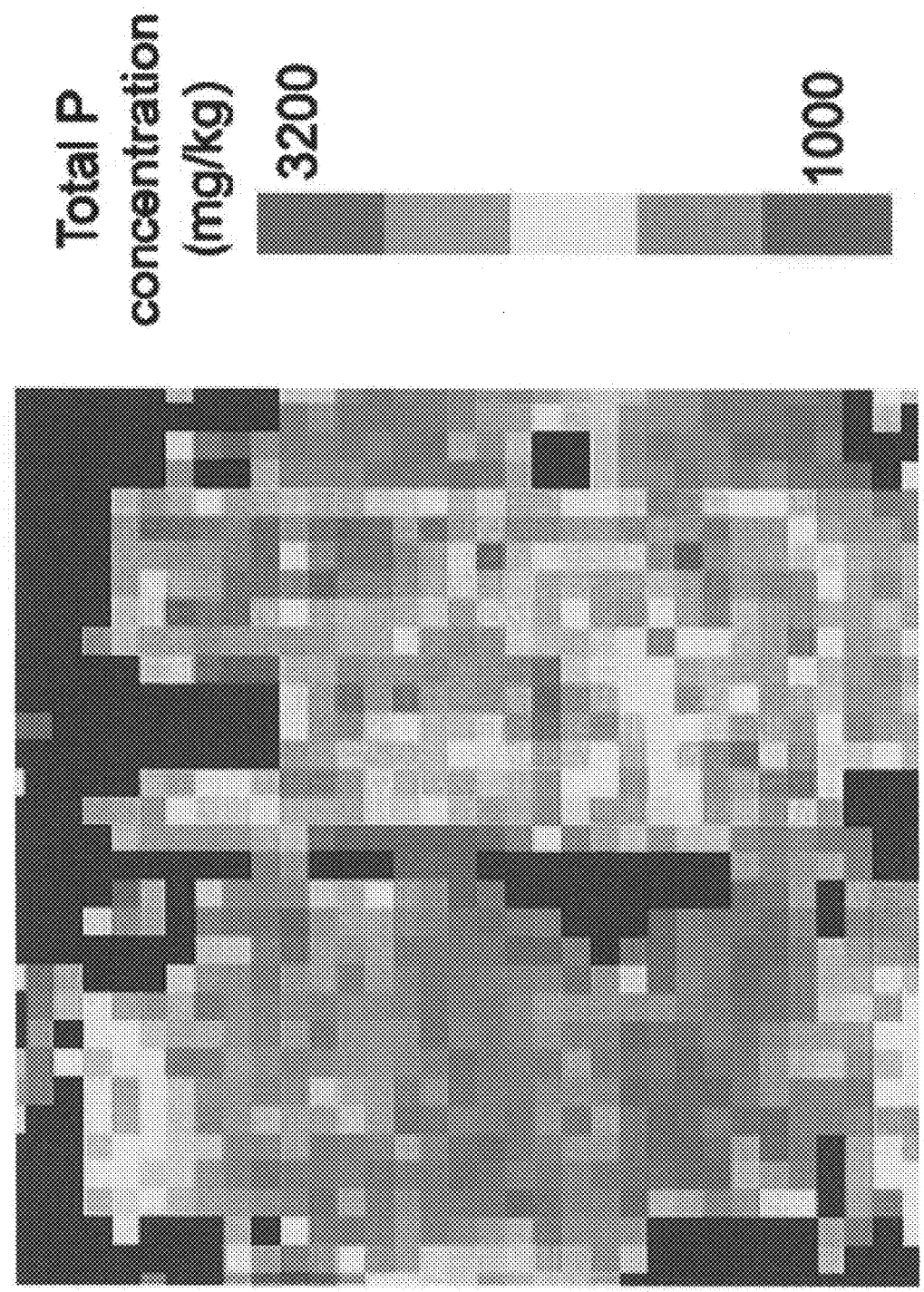
FIG. 6 is an image showing the total phosphorus concentration (mg/kg) in surface soil samples of fields F34 (left side of the image) and F11 (right side of the image), displayed as red (high phosphorus content) to turquoise (low phosphorus content), obtained by applying the phosphorus spectral ratio model to the LANDSAT 5 TM frame of Jun. 5, 2005, in accordance with one embodiment of the present invention.
Figure 7:
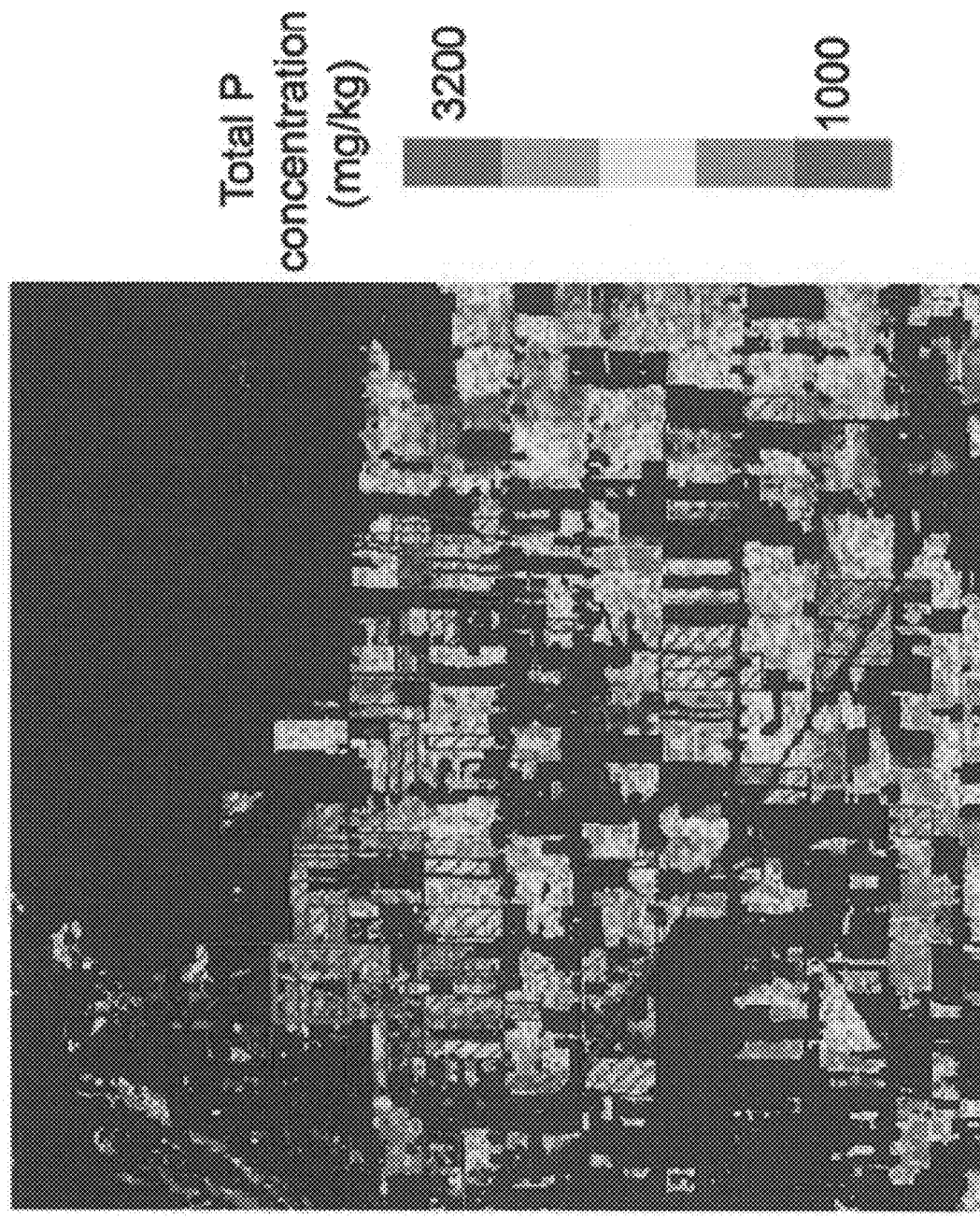
FIG. 7 is an image showing the total phosphorus concentration (mg/kg) in surface soil samples of the bare soil fields in the eastern part of the Lucas County of northwest Ohio, which is a part of the drainage basin of Lake Erie, which is located at the northern side (top) of the image, in accordance with one embodiment of the present invention.

The application of the best phosphorus spectral ratio model to the LANDSAT 5 TM frame of May 20, 2005, which was also used in developing the model, is shown in FIG. 5. The redder color in this image corresponds to higher amounts of phosphorus in surface soil. FIG. 6 shows the image of the same spectral ratio model that was developed using the LANDSAT 5 frame of May 20, 2005, being applied to the LANDSAT 5 frame of Jun. 5, 2005. Note that the phosphorus concentration in the F34 field is significantly higher than the F11 field in both the images (FIGS. 5 and 6). The application of the best phosphorus spectral ratio model to the May 20, 2005, LANDSAT TM image, showing the part of the watershed that drains into Lake Erie, is given in FIG. 7. The fields outlined in this figure are permitted for Class B biosolid application.

Discussion

The analytical results showed that the accumulation of phosphorus in surface soil samples of F34 was about 2.6 times higher than for the F11 soils. This confirms the report of Chang et al. (1983) that five continuous years of biosolids application in two California soils at 0, 22.5, 45 and 90 ton per hectare increased the total phosphorus concentration of surface soil (0-15 cm) from 515-540 mg/kg to 1092-1312, 1657-2163 and 2617-3470 mg/kg, respectively. Similarly Maguire et al. (2000) reported that the concentration of total soil phosphorus in surface soils (0-20 cm) of biosolid amended soils was 738 mg/kg, or nearly double the values in unamended soils, where the total soil phosphorus was 403 mg/kg. High concentrations of Cd and Cu in the surface soils of F34 compared to F11 agree with the reports of Nyamangara and Mzezewa (1999), that the long-term application of biosolid increases the accumulation of Cd and Cu in the surface soils.

The spectral results showed that the intensity of spectral reflectance (from 350-2500 nm spectral range) decreases with increases in phosphorus concentration of the soils (FIG. 2) agreeing with the results of Bogrekci and Lee (2005). Bogrekci and Lee (2005) also showed that the removal of phosphorus and other nutrients from soils through leaching results in an increase in the spectral reflectance of soils. In this example, the reflectance of the soil samples (FIG. 2) decreased more in the NIR region compared to the visible region. Bogrekci and Lee (2007) found a good relationship between reflectance and phosphorus concentration with coefficients of determination of 0.93, 0.95 and 0.76 for total, Mehlich-1 and water soluble phosphorus. The reflectance of F34 surface soil samples is low compared to the rest of the soil samples and this can be attributed to its high total phosphorus concentration of 2550 mg/kg (FIG. 2). LANDSAT TM data can be used to estimate and map some chemical characteristics of soils, such as total phosphate content, as shown in this example. Although not limited to the theory by which the invention operates, these results allow one to conclude that remotely sensed imagery of bare soil fields can be used to quantify and map the spatial variation of total phosphorus concentration in surface soils. The technology is simple enough to be applied to the entire watershed. The phosphorus spectral ratio model was more robust and reliable than the single band input models and can be applied to bare soil fields with low (b13%) soil moisture.

Nanni and Dematte (2006) have successfully employed LANDSAT TM data to estimate the sand, silt, clay, organic matter, cation exchange capacity (CEC) and sum of cations in Brazilian soils. They derived spectral reflectance values from the corrected LANDSAT image to develop multiple regression equations in order to estimate the different physical and chemical characteristics of the soils; however, no soil maps were presented in that study (Nanni and Dematte, 2006). The present invention is believed to be significant because it represents the first successful effort in using LANDSAT TM data to estimate and map phosphorus concentration in surface soils. The phosphorus spectral ratio model was also successfully validated by applying it to another LANDSAT image obtained on Jun. 5, 2005.

Aerial imagery was used to map the organic carbon (Chen et al., 2000), clay content (Sullivan et al., 2005), organic matter and Bray-1 phosphorus concentration (Varvel et al., 1999) and LANDSAT TM imagery was used to estimate the physical and chemical properties (Nanni and Dematte, 2006) of surface soils in the previous studies.

However, the algorithms developed in accordance with the preferred embodiment of the present invention were based on the reflected image intensity values of the soils, which required correction for atmospheric haze with atmospheric models before applying the algorithms to another date. The phosphorus spectral ratio model developed in this example is based on the DOS-corrected spectral ratios and is more robust than any model that could be derived from a combination of single spectral bands. Vincent et al. (2004) showed that the DOS spectral ratio models were more robust than single band models and can be applied with reasonable accuracy to different times of data collection, though their, subject was cyanobacteria blooms in lakes or streams, and the present example is about phosphorus concentrations in bare soils on dry land.

By applying the phosphorus spectral ratio model, one can identify and map the phosphorus concentration in surface soils as a result of biosolid application.

Because phosphorus accumulation in soils can also result from the application of biosolids, animal manures, and man-made fertilizers, this research has significant implications in identifying the fields with high concentrations of surface soil phosphorus, thus helping in the implementation of phosphorus-based management practices on agricultural fields, with an aim toward reduction of phosphorus runoff into nearby surface water bodies.

Shober and Sims (2003) reported that twenty-four of the states and territories in the United States now have regulations to restrict the land application of biosolids, based on phosphorus concentration in soil.

Thirteen of these 24 states have established actual numerical limits for soil test phosphorus (STP), with an aim to cease the application of biosolids once these limits are reached. As the total soil phosphorus and STP are linearly related to each other (Allen and Mallarino, 2006), the phosphorus spectral ratio model in accordance with the present invention can be used to monitor phosphorus levels in surface soils.

One limitation of this phosphorus model is that it was developed using bare soil fields that had low surface soil moisture (b13%). While there is currently no data respecting this model's performance on fields with soil moisture contents greater than that value, one may apply the present invention based upon this phosphorus model on fields with higher moisture contents through making adjustments to accommodate this condition, without undue experimentation. One may also apply the present invention to determine the phosphorus concentration in surface soils of other soil types in this region or other regions, though the soils tested were of the prevalent type (Latty Silty Clay).

Mapping and Estimation of Phosphorus and Copper Concentrations in Fly Ash Spill Area Using LANDSAT TM Images Introduction A vast amount of fly ash, a by-product of coal incineration, spilled over a wide area on Dec. 22, 2008, at approximately 0100 hours EST, when an earthen wall of a fly ash disposal pond broke at the Tennessee Valley Authority (TVA) Kingston Fossil Plant, located at Harriman, Roane County, Tenn. (TVA, 2009). This is the largest environmental disaster of its kind involving a coal fly ash spill in US history (New York Times, 2008). Approximately 5.4 million cubic yards of fly ash spilled over an area of 300 acres outside the ash storage ponds. Fly ash also spilled into the Emory River and the tributaries that flow into the Emory River, which serve as a source of drinking water (TVA, 2009; New York Times, 2008).

Accumulation of large amounts of fly ash as a result of coal combustion is becoming a major environmental concern in the United States. With the Nation's increasing demand for energy, the increase in coal combustion has required the disposal of large quantities of coal combustion residues.

Approximately 131 million tons of coal combustion residues were generated within the US in 2007, of which 36% was disposed in landfills, 21% in surface impoundments, and the remainder was reused for beneficial purposes. There are approximately 300 landfills and 300 surface impoundment facilities used by 440 coal-fired plants across the US.

The physical and chemical properties of the fly ash generated at a given coal-fired plant depends on the nature of the coal being burned, type of the combustion method, and the storage and handling methods involved. In general, fly ash is substantially rich in many elements (including heavy metals) and is usually stored in either landfills or artificial lagoons on open land. The general chemical composition of fly ash is given in Table 1 (Page et al., 1979). Mapping the spatial distribution of chemical concentrations as a result of fly ash spill is important for determining its effect on human and environmental health and for conducting remediation and recovery efforts. Previous studies have shown that fly ash pollution can be monitored through several methods: conventional soil sampling and analysis, measurement of Sr-87 to Sr-86 ratios in plant samples growing in the vicinity, and measurement of ferromagnetic mineral concentrations present within the fly ash by magnetic mapping. However, all of these methods are based on point measurements at the ground-level, requiring intensive sampling of large-scale contaminated areas, which is expensive, time-consuming and sometimes not even possible as the areas may be sufficiently hazardous (e.g., poor slope stability) and inaccessible to scientists and engineers.

LANDSAT TM Images

Remote sensing has been used as an alternative method for determining and mapping the physical and chemical characteristics of exposed soils. In this embodiment, LANDSAT Thematic Mapper (TM) sensor data was used to identify and map the TVA's fly ash spill in Tennessee.

LANDSAT TM is a medium-resolution, multi-spectral imager with spectral bands 1-7 covering the visible, near-infrared, and thermal regions of the electromagnetic spectrum. The spectral range of these LANDSAT TM bands are as follows: Band 1: 450-520 nm; Band 2: 520-600 nm; Band 3: 630-690 nm; Band 4: 760-900 nm; Band 5: 1,550-1,750 nm; Band 6: 10,400-12,500 nm and Band 7: 2,080-2,350 nm. The Thematic Mapper and Enhanced Thematic Mapper plus (ETM+) sensors were aboard the LANDSAT 5 and 7 respectively, each of which has a 16-day repeat cycle with a pixel size of 30 m×30 m for bands 1-5 and 7. Because the two satellites have an 8-day offset from one another, it is possible to obtain coverage of a given ground area every 8 days, though the TM sensor aboard LANDSAT 7 (called ETM+) has approximately a quarter of its pixels missing, due to the loss of its scan line converter since May 31, 2003. In order to monitor the before and after fly ash spill events of the Kingston fly ash plant, LANDSAT 5 TM data acquired on Nov. 20, 2008 (32 days before the fly ash spill), Dec. 22, 2008 (about 9 hours after the fly ash spill), and Feb. 1, 2009 (40 days after the fly ash spill) was downloaded for this embodiment. The LANDSAT TM images were then processed with the ER Mapper image processing software, a commercial product of Earth Resources Mapping, Inc.

Measuring the Chemical Concentrations from LANDSAT TM Imagery

The dark-object-subtracted (DOS) pixel values corresponding to LANDSAT TM bands 1-5 and 7 were derived from each of the images. The dark object of each spectral band is defined as one value less than the minimum digital number found in all the pixels of the image for that spectral band. The objective of this example was to show that the phosphorus and copper concentrations in the exposed fly ash and soil in the spill vicinity can be estimated and mapped using LANDSAT TM data. For this purpose, the spectral ratio models that were developed to estimate and map the phosphorus and copper concentrations in surface soil samples of sewage sludge amended soils (Sridhar et al., 2009) were applied to each of the three LANDSAT TM images covering the fly ash spill study area. The algorithms used for estimation of phosphorus and copper concentrations are as follows: P (ppm)=4156-1690 (R51)+2257 (R73); Cu (ppm)=75-17.9 (R51)+21.9 (R73), where R51 and R73 are the dark-object-subtracted (haze corrected) values of TM band 5 divided by TM band 1 and TM band 7 divided by TM band 3, respectively. The R2 (Adjusted) values and standard error for the P algorithm were 67.9% and 531 ppm, respectively, and for the Cu algorithm were 59% and 6.9 ppm. For each of the three LANDSAT TM images to which these spectral ratio models were applied, masks were created to limit the display to only bare soil fields. Details of these algorithmic models were reported elsewhere (Sridhar et al., 2009).

Results of Image Analysis

Figure 8:
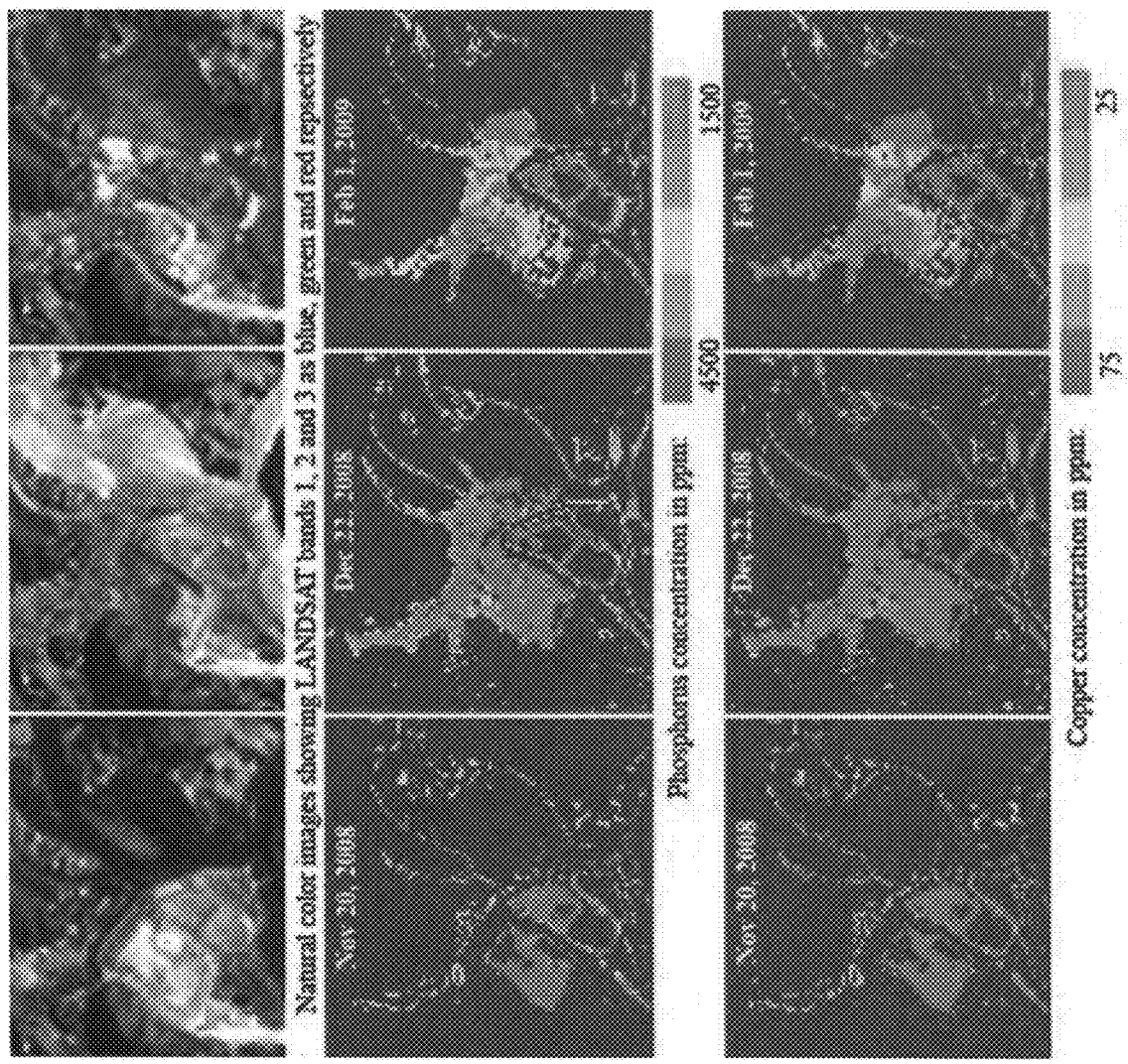
FIG. 8 shows LANDSAT TM images of a fly ash spill area acquired and analyzed in accordance with the one embodiment of the present invention.

FIG. 8 shows the natural color images, total phosphorus and copper concentration images of the fly ash-spill vicinity for each of the following dates of LANDSAT TM overpass: Nov. 20, 2008, Dec. 22, 2008, and Feb. 1, 2009, representing the periods of 32 days before the fly ash spill, 9 hours after, and 40 days after the fly ash spill, respectively. The images in rows 1-3 represent the natural color image, surface P concentration image, and surface Cu concentration image, respectively.

The fly ash is seen as a grey-colored area in the Dec. 22, 2008 natural color imagery. Image interpretation of a standard natural color image (TM bands 1, 2, and 3 displayed as blue, green, and red, respectively) yields limited success for mapping the fly ash deposits because the contrast between fly ash and background soils is small in visible wavelength regions.

The LANDSAT TM derived P concentrations range from 1,500 to 4,500 ppm and the Cu concentrations from 25 to 75 ppm in the November, 2008 and February, 2009 images.

Turquoise, yellow, orange and red colors were assigned to increasing phosphorus and copper concentrations as indicated by the respective color coding bars in FIG. 8. The intense red color in the Dec. 22, 2008 image clearly stands out due to larger areas of high phosphorus and copper concentration exposures at the surface, compared to the Nov. 20, 2008 image acquired before the fly ash spill. The 25 to 75 ppm range of Cu concentrations derived from the Dec. 22, 2008 image correlates well with the 29.9 to 69.4 ppm range of Cu values obtained through laboratory analysis from eight (8) ash sampling locations collected from Dec. 23, 2008 through Jan. 5, 2009 in the fly ash spill vicinity (Tetra Tech, 2009). The P concentrations were not reported through soil analysis (Tetra Tech, 2009).

In November, before the fly ash spill, the high concentrations of phosphorus and copper were shown to be confined to the fly ash ponds. In December, a large extent of increased phosphorus and copper concentrations is clearly evident toward the northern and northeastern side of the ash holding ponds as shown in FIG. 8. These high phosphorus and copper concentration features agree with the fly ash spill toward the northern and northeastern sides of the ash holding ponds (TVA, 2009). In February, the phosphorus and copper concentrations mapped with the same LANDSAT TM algorithms were lower than those recorded in December. As an action item for dust suppression, TVA spread 85 tons of winter rye grass, 650 tons of straw and other erosion-control mulch on the surface of the fly ash spill areas from Jan. 3 through Jan. 15, 2009 (TVA, 2009).

For areas where grass and straw were spread over, the Feb. 1, 2009 image shows lower phosphorus and copper concentrations, compared to the Dec. 22, 2008 image. This series of images shows that LANDSAT TM data can be used to quantitatively monitor the remediation and recovery efforts of phosphorus and copper contaminated sites.

CONCLUSIONS

In summary, the application of phosphorus and copper mapping algorithms from LANDSAT TM images have allowed us to map and estimate the increase in surface concentrations of these two elements as a result of fly ash spill. These results show the effective use of multispectral satellite image analysis in determining surface soil chemical concentrations.

Compared to point measurements made by ground-based soil sampling and chemical analysis, the satellite-based measurements have a great advantage in mapping the spatial distribution and concentration of elements and chemical compositions over time. As LANDSAT TM has 30-m spatial resolution, there is a measurement by the satellite for every ⅕ of an acre (the area covered by one pixel) during each overpass, which would be cost prohibitive for point measurements that require manual soil sample collection and laboratory analysis of each sample. Satellite monitoring of surface soil elemental concentrations for environmental purposes can surpass point measurements on the ground and measured in the laboratory, at least for phosphorus and copper.

The results obtained in this embodiment as regards phosphorus and copper were found to be the best compared to several other elements that were studied for similar algorithms (Sridhar et al., 2009). However, with more and better suited spectral bands, future satellites hold the promise of enabling us to move beyond the point-based in situ measurements provided by soil sampling, except for checks on the satellite algorithms that measure surface elemental and chemical compound concentrations from the spectral behavior of their reflectance of sunlight and emittance of heat from the Earth's surface.

Additional background for the invention is provided by the following references which are hereby incorporated by reference.

REFERENCES

1. Allen B L, Mallarino A P. Relationships between extractable soil phosphorus and phosphorus saturation after long-term fertilizer or manure application. Soil Sci Soc Am J 2006; 70:454-63.
2. Ben-Dor E, Banin A. Near infrared reflectance analysis of carbonate concentration in soils. Appl Spectrosc 1990; 44:1064-9.
3. Ben-Dor E, Banin A. Near infrared analysis (NIRA) as a method to simultaneously evaluate spectral featureless constituents in soils. Soil Sci 1995; 4:259-70.
4. Bergkvist P, Jarvis N, Berggren D, Carlgren K. Long-term effects of sewage sludge applications on soil properties, cadmium availability and distribution in arable soil. Agric Ecosyst Environ 2003; 97:167-79.
5. Bogrekci I, Lee W S. Spectral soil signatures and sensing phosphorus. Biosyst Eng 2005; 92:527-33.

6. Bogrekci I, Lee W S. Comparison of ultraviolet, visible and near infrared sensing for soil phosphorus. Biosyst Eng 2007; 96:293-9.
7. Chang A C, Page A L, Sutherland F H, Grgurevic E. Fractionation of phosphorus in sludge affected soils. J Environ Qual 1983; 12:286-90.
8. Chang C W, Laird D A, Mausbach M J, Hurburgh Jr C R. Near-infrared reflectance spectroscopy-principal component regression analysis of soil properties. Soil Sci Soc Am J 2001; 65:480-90.
9. Chen F, Kissel D E, West L T, Adkins W. Field-scale mapping of surface soil organic carbon using remotely sensed imagery. Soil Sci Soc Am J 2000; 64:746-53.
10. Dalal R C, Henry R J. Simultaneous determination of moisture, organic carbon, and total nitrogen by near infrared reflectance spectrophotometry. Soil Sci Soc Am J 1986; 50:120-3.
11. Dematte J A M, Pereira H S, Nanni M R, Cooper M, Fiora P R. Soil chemical alterations promoted by fertilizer application assessed by spectral reflectance. Soil Sci 2003; 168: 730-47.
12. Durbin J, Watson G S. Testing for serial correlation in least squares regression: II. Biometrica 1951; 38:159-78.
13. Epstein E, Taylor J M, Chaney R L. Effects of sewage sludge on some soil physical properties. J Environ Qual 1975; 4:139-42.
14. Henderson T L, Baumgardner M F, Franzmeieir D P, Stott D E, Coster D C. High dimensional reflectance analysis of soil organic matter. Soil Sci Soc Am J 1992; 56:865-72.
15. Ji J F, Balsam W L, Chen J, Liu L W. Rapid and quantitative measurement of hematite and goethite in the Chinese Loess-Paleosol sequence by diffuse reflectance spectroscopy. Clay Miner 2002; 50:208-16.
16. Lobell D B, Asner G P. Moisture effects on soil reflectance. Soil Sci SocAmJ 2002; 66:722-7.
17. Maguire R O, Sims J T, Coale F J. Phosphorus fractionation in biosolids-amended soils: relationship to soluble and desorbable phosphorus. Soil Sci SocAmJ 2000; 64:2018-24.
18. Mantovi P, Baldoni G, Toderi G. Reuse of liquid, desoiled, and composted sewage sludge on agricultural land: effects of long-term application on soil and crop. Soil Res 2005; 39:289-96.
19. McNulty, W. S. The creation of a GIS database and the determination of sludge's spectral signature in an agricultural setting. M.S. Thesis. Department of Geology, Bowling Green State University, Bowling Green, Ohio, USA, 2005.
20. MINITAB Statistical Software. Version 15. State College, Pa.: MINITAB Inc.; 2007-2008.
21. Morra M J, Hall M H, Freeborn L L. Carbon and nitrogen analysis of soil fractions using near infrared reflectance spectroscopy. Soil Sci Soc Am J 1991; 55:288-91.
22. Nanni M R, Dematte J A M. Spectral reflectance methodology in comparison to traditional soil analysis. Soil Sci Soc Am J 2006; 70:393-407.
23. Nyamangara J, Mzezewa J. The effect of long-term sewage sludge application on Zn, Cu, Ni and Pb levels in a clay loam soil under pasture grass in Zimbabwe. Agric Ecosyst Environ 1999; 73:199-204.
24. Post D F, Fimbres A, Matthias A D, Sano E E, Accioly L, Batchily A K, et al. Predicting soil albedo from soil color and spectral reflectance data. Soil Sci Soc Am J 2000; 64:1027-34.
25. Reeves III J B, McCarty G W, Mimmo T. The potential of diffuse refleCtance spectroscopy for the determination of carbon inventories in soil. Environ Pollut 2002; 116: S264-77.
26. SAS Institute. SAS Software Version 9.1. Cary, N.C.: SAS Institute, Inc.; 2002-2003.
27. Shober A L, Sims J T. Phosphorus restrictions for land application of biosolids: current status and future trends. J Environ Qual 2003; 32:1955-64.
28. Singh R P, Agrawal M. Potential benefits and risks of land application of sewage sludge. Waste Manage 2008; 28:347-58.
29. Soil Survey Staff. Natural resources conservation service. Web soil survey. United States Department of Agriculture; 2007. http://websoilsurvey.nrcs.usda.gov.
30. Sommers L E. Chemical composition of sewage sludges and analysis of their potential use as fertilizers. J Environ Qual 1977; 6:225-32.
31. Sullivan D G, Shaw J N, Rickman D. IKONOS imagery to estimate surface soil property variability in two Alabama physiographies. Soil Sci Soc Am J 2005; 69:1789-98.
32. Udom B E, Mbagwu J S C, Adesodun J K, Agbim N N. Distributions of zinc, copper, cadmium and lead in a tropical ultisol after long-term disposal of sewage sludge. Environ Int 2004; 30:467-70.
33. U.S. Environmental Protection Agency. Test methods for evaluating solid waste. Office of Solid Waste and Emergency Response, Washington D.C; 1998.
34. U.S. Environmental Protection Agency. Standards for the use or disposal of sewage sludge. Office of Soil, Washington D.C; 2002.
35. Varvel G E, Schlemmer M R, Schepers J S. Relationship between spectral data from an aerial image and soil organic matter and phosphorus levels. Precis Agric 1999; 1:291-300.
36. Vincent R K. Fundamentals of geological and environmental remote sensing. Upper Saddle River, N.J.: Prentice Hall; 1997.
37. Vincent R K. Forecasts of monthly averaged daily temperature highs in Bowling Green, Ohio from monthly sea surface temperature anomalies in Eastern Pacific ocean during the previous year. Photogramm Eng Remote Sensing 2000; 66:1001-9.
38. Vincent R K, Qin X, McKay R M L, Miner J, Czajkowski K, Savino J, et al. detection from LANDSAT TM data for mapping cyanobacterial blooms in Lake Erie. Remote Sens Environ 2004; 89:381-92.
39. Wei Q F, Lowery B, Peterson A E. Effect of sludge application on physical properties of a silty clay loam soil. J Environ Qual 1985; 14:178-80.
40. New York Times, 2008. Tennessee ash flood larger than initial estimate, Published on Dec. 26, 2008, URL: http://www.nytimes.com/2008/12/27/us/27sludge.html?_r=2&ref=us (last date accessed: 1 Jul. 2009).
41. Page, A. L., A. A. Elseewi, and I. R. Straughan, 1979. Physical and chemical properties of fly ash from coal-fired power plants with special reference to environmental impacts, Residue Reviews, Vol. 71, pp. 83-120.
42. Sridhar, B. B. M., R. K. Vincent, J. D. Witter, and A. J. Spongberg, 2009. Mapping the total phosphorus concentration of biosolid amended surface soils using LANDSAT TM data, Science of Total Environment, Vol. 47, pp. 2894-2899.
43. Tennessee Valley Authority, 2009. Corrective Action Plan for the TVA Kingston Fossil Plant Ash Release; 2009, URL: http://www.tva.gov/kingston/cap/TVA_Corrective_Action_Plan_Draft_D5.pdf (last date accessed: 1 Jul. 2009).

44. Tetra Tech EM Inc, 2009. Final CERCLA emergency response report, Kingston fossil plant Fly ash response Harriman, Roane County, Tennessee Tetra Tech Inc. Soil and ash sampling results Kingston fossil fly ash response Harriman, Roane County, Tennessee; 2009, URL: http://www.epaosc.org/sites/4642/files/erfinal reporttvakingston.pdf (last date accessed: 1 Jul. 2009).

Having shown and described a preferred embodiment of the invention, those skilled in the art will realize that many variations and modifications may be made to affect the described invention and still be within the scope of the claimed invention. Thus, many of the elements indicated above may be altered or replaced by different elements which will provide the same result and fall within the spirit of the claimed invention. It is the intention, therefore, to limit the invention only as indicated by the scope of the claims.

What is claimed is:

1. A method of measuring phosphorus in soil from light reflected therefrom, said method comprising the steps of:
   (a) obtaining a measurement of reflected light from said soil using a light measurement device, said measurement comprising a measurement of the respective amount of light in at least two wavelength ranges; and
   (b) determining the approximate amount of phosphorus in said soil from said respective amounts of light by applying an algorithm using a microprocessor to relate said respective amounts of light in said at least two wavelength ranges to the amount of phosphorus in said soil, wherein said algorithm comprises a ratio of the respective amount of light in said at least two wavelength ranges.

2. A method according to claim 1 wherein said at least two wavelength ranges comprises four wavelength ranges.

3. A method according to claim 2 wherein said algorithm comprises a ratio of the respective amount of light in a first pair of said four wavelength ranges, and a ratio of the respective amount of light in a second pair of said four wavelength ranges.

4. A method according to claim 1, wherein said method comprises the steps of:
   (a) obtaining a measurement of reflected light from said soil using a light measurement device, said measurement comprising a measurement of the respective amount of light in at least four wavelength ranges: (i) Band 1 from about 0.45 µm to about 0.52 µm; (ii) Band 3 from about 0.63 µm to about 0.69 µm; (iii) Band 5 from about 1.55 µm to about 1.75 µm; and (iv) Band 7 from about 2.08 µm to about 2.35 µm; and
   (b) determining the approximate amount of phosphorus in said soil from said respective amounts of light by applying an algorithm using a microprocessor, using a microprocessor relating said respective amounts of light in said at least four wavelength ranges to the amount of phosphorus in said soil.

5. A method according to claim 4 wherein said algorithm is selected from the group consisting of P (mg/kg)=$K_1$−$K_2$ (R51)+$K_3$ (R73) wherein P is the amount of phosphorus expressed in milligrams per kilogram; $K_1$, $K_2$, and $K_3$ are constants; R51 is a ratio of the amount of reflected light in Band 5 to the amount of reflected light in Band 1; and R73 is a ratio of the amount of reflected light in Band 7 to the amount of reflected light in Band 3, and mathematical equivalents thereof.

6. A method according to claim 5 wherein:
   $K_1$ is a value in the range of from about 4000 to about 4300;
   $K_2$ is a value in the range of from about 1600 to about 1780;
   $K_3$ is a value in the range of from about 2150 to about 2350.

7. A method according to claim 6 wherein:
   $K_1$ is a value in the range of from about 4100 to about 4200;
   $K_2$ is a value in the range of from about 1650 to about 1700;
   $K_3$ is a value in the range of from about 2200 to about 2300.

8. A method according to claim 7 wherein
   $K_1$ is a value of about 4156±3;
   $K_2$ is a value of about 1690±3;
   $K_3$ is a value of about 2257±3.

9. A method according to claim 1 wherein said additionally comprising the step of transmitting data relating to the approximate amount of said phosphorus to a site remote from the site where said measurement takes place.

10. A method according to claim 1 additionally comprising the step of generating a report of said approximate amount of said phosphorus in said soil.

11. A system for measuring phosphorus in soil from light reflected therefrom, said system comprising:
    (a) a measurement device adapted to measure reflected light from said soil, said measurement device adapted to measure the respective amount of light in at least two wavelength ranges; and
    (b) a microprocessor capable of relating the approximate amount of said phosphorus in said soil to said respective amounts of light by applying an algorithm relating said respective amounts of light in said at least two wavelength ranges to the amount of phosphorus in said soil, wherein said algorithm comprises a ratio of the respective amount of light in said at least two wavelength ranges.

12. A system according to claim 11 wherein said at least two wavelength ranges comprises four wavelength ranges.

13. A system according to claim 12 wherein said algorithm comprises a ratio of the respective amount of light in a first pair of said four wavelength ranges, and a ratio of the respective amount of light in a second pair of said four wavelength ranges.

14. A system according to claim 11, said system comprising:
    (a) a measurement device adapted to measure reflected light from said soil, said measurement device adapted to measure the respective amount of light in at least four wavelength ranges: (i) Band 1 from about 0.45 µm to about 0.52 µm; (ii) Band 3 from about 0.63 µm to about 0.69 µm; (iii) Band 5 from about 1.55 µm to about 1.75 µm; and (iv) Band 7 from about 2.08 µm to about 2.35 µm; and
    (b) a microprocessor capable of relating the approximate amount of said phosphorus in said soil to said respective amounts of light by applying an algorithm relating said respective amounts of light in said at least four wavelength ranges to the amount of phosphorus in said soil.

15. A system according to claim 14 wherein said algorithm is selected from the group consisting of P (mg/kg)=$K_1$−$K_2$ (R51)+$K_3$ (R73) wherein P is the amount of phosphorus expressed in milligrams per kilogram; $K_1$, $K_2$, and $K_3$ are constants; R51 is a ratio of the amount of reflected light in Band 5 to the amount of reflected light in Band 1; and R73 is a ratio of the amount of reflected light in Band 7 to the amount of reflected light in Band 3, and mathematical equivalents thereof.

16. A system according to claim 15 wherein:
    $K_1$ is a value of about 4156±3;
    $K_2$ is a value of about 1690±3;
    $K_3$ is a value of about 2257±3.

17. A system according to claim 11 additionally comprising a transmitter adapted to transmit data relating to the approximate amount of said phosphorus in said soil from said microprocessor to a site remote from the site where said measurement takes place.

18. A system for measuring phosphorus in soil from light reflected therefrom, said system comprising:
 (a) a satellite comprising a measurement device adapted to measure reflected light from said soil, said measurement device adapted to measure the respective amount of light in at least two wavelength ranges; and
 (b) a microprocessor in data communication with said satellite and capable of determining the approximate amount of said phosphorus in said soil to said respective amounts of light by applying an algorithm relating said respective amounts of light in said at least two wavelength ranges to the amount of phosphorus in said soil, wherein said algorithm comprises a ratio of the respective amount of light in said at least two wavelength ranges.

\* \* \* \* \*